US009695473B2

(12) United States Patent
An et al.

(10) Patent No.: US 9,695,473 B2
(45) Date of Patent: Jul. 4, 2017

(54) GENOTYPING METHOD

(71) Applicant: GENOMICTREE, INC., Daejeon (KR)

(72) Inventors: Sung Whan An, Daejeon (KR); Myung Sok Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 26 days.

(21) Appl. No.: 14/811,396

(22) Filed: Jul. 28, 2015

(65) Prior Publication Data
US 2015/0322509 A1  Nov. 12, 2015

Related U.S. Application Data

(62) Division of application No. 13/510,226, filed as application No. PCT/KR2010/008055 on Nov. 15, 2010.

(30) Foreign Application Priority Data

Nov. 16, 2009  (KR) .................. 10-2009-0110331

(51) Int. Cl.
*C12Q 1/68* (2006.01)
*C12Q 1/70* (2006.01)

(52) U.S. Cl.
CPC ......... *C12Q 1/6874* (2013.01); *C12Q 1/6869* (2013.01); *C12Q 1/6886* (2013.01); *C12Q 1/701* (2013.01); *C12Q 1/708* (2013.01); *C12Q 1/68* (2013.01); *C12Q 2525/185* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 6,004,826 | A  | 12/1999 | Segev |
| 7,323,305 | B2 | 1/2008  | Leamon et al. |
| 8,603,749 | B2 | 12/2013 | Gillevet |
| 2004/0029251 | A1 | 2/2004 | Hoffman et al. |
| 2004/0203008 | A1 | 10/2004 | Uemori et al. |
| 2006/0177833 | A1 | 8/2006 | Brenner |
| 2008/0131937 | A1 | 6/2008 | Schroeder |
| 2009/0006002 | A1 | 1/2009 | Honisch et al. |
| 2009/0170713 | A1 | 7/2009 | van Eijk et al. |

FOREIGN PATENT DOCUMENTS

| WO | 02068684 A2 | 9/2002 |
| WO | 2008061193 A2 | 5/2008 |
| WO | 2009049889 A1 | 4/2009 |

OTHER PUBLICATIONS

Hoffman et al. (DNA bar coding and pyrosequencing to identify rare HIV drug resistance mutations, Nucleic Acids Res. 2007;35(13):e91. Epub Jun. 18, 2007).*

Binladen et al. (The Use of Coded PCR Primers Enables High-Throughput Sequencing of Multiple Homolog Amplification Products by 454 Parallel Sequencing, PLoS ONE. 2007; 2(2): e197. Published online Feb. 14, 2007).*
Extended European Search Report, Apr. 24, 2013.
Japanese Office Action, Feb. 25, 2014.
Binladen, Jonas, et al.; "The Use of Coded PCR Primers Enables High-Throughput Sequencing of Multiple Homolog Amplification Products by 454 Parallel Sequencing," PLOS ONE, 2007, pp. 1-9.
Gharizadeh, Baback, et al.; "Typing of Human Papillomavirus by Pyrosequencing," Laboratory Investigation, 2001, pp. 673-679, vol. 81.
DuFort, Sandrine, et al.; "Pyrosequencing method to detect KRAS mutation in the formalin-fixed and paraffin-embedded tumor tissues," Analytical Biochemistry, 2009, pp. 166-168, vol. 391.
Nakamura, Shota, et al.,; "Direct Metagenomic Detection of Viral Pathogens in Nasal and Fecal Specimens Using an Unbiased High-Throughput Sequencing Approach," PLOS ONE, 2009, pp. e4219-1, vol. 4.
Frank, Daniel N.,; "BARCRAWL and BARTAB: software tools for the design and implementation of barcoded primers for highly multiplexed DNA sequencing," BMC Bioinformatics, 2009, pp. 1-13, vol. 10.
Salazar, N.M., et al., "Nucleic acid scanning-by-hybridization of enterohemorrhagic *Escherichia coli* isolates using oligodeoxynucleotide arrays," Nucleic Acids Research, 1996, pp. 5056-5057, vol. 24.
Troesch, A., et al., "*Mycobacterium* Species Identification and Rifampin Resistance Testing with High-Density DNA Probe Arrays," Journal of Clinical Microbiology, 1999, pp. 49-55, vol. 37.
Lashkari, Deval A., et al, "Yeast microarrays for genome wide parallel genetic and gene expression analysis," Proc. Natl. Acad. Sci., 1997, pp. 13057-13062, vol. 94.
Travasso, Cheryl M., et al., "Human papillomavirus genotyping by multiplex pyrosequencing in cervical cancer patients from India," Journal of Biosciences, 2008, pp. 73-80, vol. 33.
Gharizadeh, Baback, et al, "Sentinel-base DNA genotyping using multiple sequencing primers for high-risk human papillomaviruses," Molecular and Cellular Probes, 2006, pp. 230-238, vol. 20.
Hoffmann, Christian, et al, "DNA bar coding and pyrosequencing to identify rare HIV drug resistance mutations," Nucleic Acids Research, 2007, pp. 1-8, vol. 35.
Anderson, Erik P., et al, "A system for multiplexed direct electrical detection of DNA synthesis," Sensors and Actuators B, 2008, pp. 79-86, vol. 129.
Aydin, Atakan, et al, New universal primers facilitate Pyrosequencing™, Electrophoresis, 2006, pp. 394-397, vol. 27.

(Continued)

*Primary Examiner* — Aaron Priest
(74) *Attorney, Agent, or Firm* — Hultquist, PLLC; Steven J. Hultquist

(57) ABSTRACT

The present invention relates to a genotyping method, and more particularly to an ID sequence, which is assigned to each genotype, and a multiplex genotyping method which uses the ID sequence. When pyrosequencing is performed using the ID sequence, a unique and simple pyrogram can be obtained for each genotype. Thus, the use of the ID sequence makes it possible to genotype viral genes, disease genes, bacterial genes and identification genes in a simple and efficient manner. In addition, a genotyping primer of the invention can be used in various genotyping methods which are performed using dispensation orders and sequencing methods.

5 Claims, 21 Drawing Sheets

(56) References Cited

OTHER PUBLICATIONS

Mohamed, Mohamed-Eslam F., et al, "Interpopulation Variation Frequency of Human Inosine 5'-Monophosphate Dehydrogenase Type II (IMPDH2) Genetic Polymorphisms," Genetic Testing, 2008, pp. 513-516, vol. 12.
Trama, Jason P., et al, "Identification and genotyping of molluscum contagiosum virus from genital swab samples by real-time PCR and Pyrosequencing," Journal of Clinical Virology, 2007, pp. 325-329, vol. 40.
Ringquist, Steven, et al, "Web-Based Primer Design Software for Genome-Scale Genotyping by Pyrosequencing®," Methods in Molecular Biology, 2007, pp. 25-38, vol. 373.
Smith, Andrew M., et al, "Quantitative phenotyping via deep barcode sequencing," Genome Research, 2009, pp. 1836-1842, vol. 19.
Parameswaran, Poornima, et al, "A pyrosequencing-tailored nucleotide barcode design unveils opportunities for large-scale sample multiplexing," Nucleic Acids Research, 2007, vol. 35: e130.
Qiu, Fang, et al., "DNA Sequence-Based "Bar Codes" for Tracking the Origins of Expressed Sequence Tags from a Maize cDNA Library Constructed Using Multiple mRNA Sources," Plant Physiology, 2003, pp. 475-481, vol. 133.
Gharizadeh, Baback, et al. "Large-scale Pyrosequencing of synthetic DNA: A comparison with results from Sanger dideoxy sequencing," Electrophoresis, 2006, pp. 3042-3047, vol. 27.
Hamady, Micah, et al., "Microbial community profiling for human microbiome projects: Tools, techniques, and challenges," Genome Research, 2009, pp. 1141-1152, vol. 19.
Fan, et al., "Parallel Genotyping of Human SNPs Using Generic High-density Oligonucleotide Tag Arrays," Genome Res., 2000, pp. 853-860, vol. 10.

\* cited by examiner

1) *KRAS* mutation types 2) general pyrosequencing and results

3) KRAS mutation difficult to detect by general pyrosequencing technique

SEQUENCE LISTING

<160> NUMBER OF SEQ ID NOS: 55

<210> SEQ ID NO 1
<211> LENGTH: 22
<212> TYPE: DNA
<213> ORGANISM: Human papillomavirus type 16

<400> SEQUENCE: 1
tgtcattatg tgctgccata tc                                          22

<210> SEQ ID NO 2
<211> LENGTH: 20
<212> TYPE: DNA
<213> ORGANISM: Human papillomavirus type 58

<400> SEQUENCE: 2
actgaagtaa ctaaggaagg                                             20

<210> SEQ ID NO 3
<211> LENGTH: 19
<212> TYPE: DNA
<213> ORGANISM: Human papillomavirus type 16

<400> SEQUENCE: 3
acagtctcct gtacctggg                                              19

<210> SEQ ID NO 4
<211> LENGTH: 21
<212> TYPE: DNA
<213> ORGANISM: Human papillomavirus type 33

<400> SEQUENCE: 4
tatgcacaca agtaactagt g                                           21

<210> SEQ ID NO 5
<211> LENGTH: 18
<212> TYPE: DNA
<213> ORGANISM: Human papillomavirus type 20

<400> SEQUENCE: 5
tgactttatg tgctgagg                                               18

<210> SEQ ID NO 6
<211> LENGTH: 20
<212> TYPE: DNA
<213> ORGANISM: Human papillomavirus type 35

<400> SEQUENCE: 6
tgttctgctg tgtcttctag                                             20

```
<210> SEQ ID NO 7
<211> LENGTH: 20
<212> TYPE: DNA
<213> ORGANISM: Human papillomavirus type 45

<400> SEQUENCE: 7
ccaagtacat atgaccctac                                              20

<210> SEQ ID NO 8
<211> LENGTH: 20
<212> TYPE: DNA
<213> ORGANISM: Human papillomavirus type 23

<400> SEQUENCE: 8
actgccactg ctgcggtttc                                              20

<210> SEQ ID NO 9
<211> LENGTH: 19
<212> TYPE: DNA
<213> ORGANISM: Human papillomavirus type 31

<400> SEQUENCE: 9
caattgcaaa cagtgatac                                               19

<210> SEQ ID NO 10
<211> LENGTH: 21
<212> TYPE: DNA
<213> ORGANISM: Human papillomavirus type 39

<400> SEQUENCE: 10
agagtcttcc ataccttcta c                                            21

<210> SEQ ID NO 11
<211> LENGTH: 21
<212> TYPE: DNA
<213> ORGANISM: Human papillomavirus type 56

<400> SEQUENCE: 11
tactgctaca gaacagttaa g                                            21

<210> SEQ ID NO 12
<211> LENGTH: 22
<212> TYPE: DNA
<213> ORGANISM: Human papillomavirus type 59

<400> SEQUENCE: 12
tgtgctctac tactctctat tc                                           22

<210> SEQ ID NO 13
<211> LENGTH: 20
<212> TYPE: DNA
<213> ORGANISM: Human papillomavirus type 68

<400> SEQUENCE: 13
actactgaat cagctgtacc                                              20

<210> SEQ ID NO 14
<211> LENGTH: 23
<212> TYPE: DNA
<213> ORGANISM: Human papillomavirus type 66

<400> SEQUENCE: 14
actattaatg cagctaaaag cac                                          23
```

-continued

<210> SEQ ID NO 15
<211> LENGTH: 20
<212> TYPE: DNA
<213> ORGANISM: Human papillomavirus type 82

<400> SEQUENCE: 15
tgttactcca tctgttgcac                                              20

<210> SEQ ID NO 16
<211> LENGTH: 50
<212> TYPE: DNA
<213> ORGANISM: Artificial Sequence
<220> FEATURE:
<223> OTHER INFORMATION: Synthetic Construct

<400> SEQUENCE: 16
taatacgact cactataggg agcacatgtg tcattatgtg ctgccatatc              50

<210> SEQ ID NO 17
<211> LENGTH: 48
<212> TYPE: DNA
<213> ORGANISM: Artificial Sequence
<220> FEATURE:
<223> OTHER INFORMATION: Synthetic Construct

<400> SEQUENCE: 17
taatacgact cactataggg tgcacatgac tgaagtaact aaggaagg                48

<210> SEQ ID NO 18
<211> LENGTH: 47
<212> TYPE: DNA
<213> ORGANISM: Artificial Sequence
<220> FEATURE:
<223> OTHER INFORMATION: Synthetic Construct

<400> SEQUENCE: 18
taatacgact cactataggg cgcacatgac agtctcctgt acctggg                 47

<210> SEQ ID NO 19
<211> LENGTH: 49
<212> TYPE: DNA
<213> ORGANISM: Artificial Sequence
<220> FEATURE:
<223> OTHER INFORMATION: Synthetic Construct

<400> SEQUENCE: 19
taatacgact cactataggg gacacatgta tgcacacaag taactagtg               49

<210> SEQ ID NO 20
<211> LENGTH: 46
<212> TYPE: DNA
<213> ORGANISM: Artificial Sequence
<220> FEATURE:
<223> OTHER INFORMATION: Synthetic Construct

<400> SEQUENCE: 20
taatacgact cactataggg gtcacatgtg actttatgtg ctgagg                  46

<210> SEQ ID NO 21
<211> LENGTH: 48
<212> TYPE: DNA
<213> ORGANISM: Artificial Sequence
<220> FEATURE:
<223> OTHER INFORMATION: Synthetic Construct

<400> SEQUENCE: 21
taatacgact cactataggg gcgacatgtg ttctgctgtg tcttctag        48

<210> SEQ ID NO 22
<211> LENGTH: 48
<212> TYPE: DNA
<213> ORGANISM: Artificial Sequence
<220> FEATURE:
<223> OTHER INFORMATION: Synthetic Construct

<400> SEQUENCE: 22
taatacgact cactataggg gctacatgcc aagtacatat gaccctac        48

<210> SEQ ID NO 23
<211> LENGTH: 48
<212> TYPE: DNA
<213> ORGANISM: Artificial Sequence
<220> FEATURE:
<223> OTHER INFORMATION: Synthetic Construct

<400> SEQUENCE: 23
taatacgact cactataggg gcatcatgac tgccactgct gcggtttc        48

<210> SEQ ID NO 24
<211> LENGTH: 47
<212> TYPE: DNA
<213> ORGANISM: Artificial Sequence
<220> FEATURE:
<223> OTHER INFORMATION: Synthetic Construct

<400> SEQUENCE: 24
taatacgact cactataggg gcagcatgca attgcaaaca gtgatac        47

<210> SEQ ID NO 25
<211> LENGTH: 49
<212> TYPE: DNA
<213> ORGANISM: Artificial Sequence
<220> FEATURE:
<223> OTHER INFORMATION: Synthetic Construct

<400> SEQUENCE: 25
taatacgact cactataggg gcactatgag agtcttccat accttctac       49

<210> SEQ ID NO 26
<211> LENGTH: 49
<212> TYPE: DNA
<213> ORGANISM: Artificial Sequence
<220> FEATURE:
<223> OTHER INFORMATION: Synthetic Construct

<400> SEQUENCE: 26
taatacgact cactataggg gcacgatgta ctgctacaga acagttaag       49

<210> SEQ ID NO 27
<211> LENGTH: 50
<212> TYPE: DNA
<213> ORGANISM: Artificial Sequence
<220> FEATURE:
<223> OTHER INFORMATION: Synthetic Construct

<400> SEQUENCE: 27
taatacgact cactataggg gcacactgtg tgctctacta ctctctattc      50

```
<210> SEQ ID NO 28
<211> LENGTH: 48
<212> TYPE: DNA
<213> ORGANISM: Artificial Sequence
<220> FEATURE:
<223> OTHER INFORMATION: Synthetic Construct

<400> SEQUENCE: 28
taatacgact cactataggg gcacagtgac tactgaatca gctgtacc              48

<210> SEQ ID NO 29
<211> LENGTH: 51
<212> TYPE: DNA
<213> ORGANISM: Artificial Sequence
<220> FEATURE:
<223> OTHER INFORMATION: Synthetic Construct

<400> SEQUENCE: 29
taatacgact cactataggg gcacatagac tattaatgca gctaaaagca c           51

<210> SEQ ID NO 30
<211> LENGTH: 48
<212> TYPE: DNA
<213> ORGANISM: Artificial Sequence
<220> FEATURE:
<223> OTHER INFORMATION: Synthetic Construct

<400> SEQUENCE: 30
taatacgact cactataggg gcacatcgtg ttactccatc tgttgcac              48

<210> SEQ ID NO 31
<211> LENGTH: 23
<212> TYPE: DNA
<213> ORGANISM: Artificial Sequence
<220> FEATURE:
<223> OTHER INFORMATION: Synthetic Construct

<400> SEQUENCE: 31
tttgttactg tggtagatac tac                                         23

<210> SEQ ID NO 32
<211> LENGTH: 25
<212> TYPE: DNA
<213> ORGANISM: Artificial Sequence
<220> FEATURE:
<223> OTHER INFORMATION: Synthetic Construct

<400> SEQUENCE: 32
gaaaaataaa ctgtaaatca tattc                                       25

<210> SEQ ID NO 33
<211> LENGTH: 9
<212> TYPE: DNA
<213> ORGANISM: Homo sapiens

<400> SEQUENCE: 33 tggagctgt                                                          9

<210> SEQ ID NO 34
<211> LENGTH: 9
<212> TYPE: DNA
<213> ORGANISM: Homo sapiens

<400> SEQUENCE: 34 gagctggtt                                                          9
```

```
<210> SEQ ID NO 35
<211> LENGTH: 9
<212> TYPE: DNA
<213> ORGANISM: Homo sapiens

<400> SEQUENCE: 35 agctggtgc                                                                  9

<210> SEQ ID NO 36
<211> LENGTH: 36
<212> TYPE: DNA
<213> ORGANISM: Artificial Sequence
<220> FEATURE:
<223> OTHER INFORMATION: Synthetic Construct

<400> SEQUENCE: 36
aacttgtggt agttggagct gtgcagttgg agctgt                                   36

<210> SEQ ID NO 37
<211> LENGTH: 36
<212> TYPE: DNA
<213> ORGANISM: Artificial Sequence
<220> FEATURE:
<223> OTHER INFORMATION: Synthetic Construct

<400> SEQUENCE: 37
aacttgtggt agttggagct gtgctgtgag ctggtt                                   36

<210> SEQ ID NO 38
<211> LENGTH: 37
<212> TYPE: DNA
<213> ORGANISM: Artificial Sequence
<220> FEATURE:
<223> OTHER INFORMATION: Synthetic Construct

<400> SEQUENCE: 38
aacttgtggt agttggagct cgcacattag ctggtgc                                  37

<210> SEQ ID NO 39
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: n is a, c, g, or t

<400> SEQUENCE: 39
nnnggcctgc tgaaaatgac tgaa                                                24

<210> SEQ ID NO 40
<211> LENGTH: 24
<212> TYPE: DNA
<213> ORGANISM: Artificial Sequence
<220> FEATURE:
<223> OTHER INFORMATION: Synthetic Construct

<400> SEQUENCE: 40
ttagctgtat cgtcaaggca ctct                                                24

<210> SEQ ID NO 41
<211> LENGTH: 24
<212> TYPE: DNA
<213> ORGANISM: Artificial Sequence
```

```
<220> FEATURE:
<223> OTHER INFORMATION: Synthetic Construct

<400> SEQUENCE: 41
atatacaaca ggatgggggc tgtg                                          24

<210> SEQ ID NO 42
<211> LENGTH: 25
<212> TYPE: DNA
<213> ORGANISM: Artificial Sequence
<220> FEATURE:
<223> OTHER INFORMATION: Synthetic Construct

<400> SEQUENCE: 42
atcatcatcc caggcgacaa agatg                                         25

<210> SEQ ID NO 43
<211> LENGTH: 28
<212> TYPE: DNA
<213> ORGANISM: Artificial Sequence
<220> FEATURE:
<223> OTHER INFORMATION: Synthetic Construct

<400> SEQUENCE: 43
tgatatgcct ataacaaatg accagaaa                                      28

<210> SEQ ID NO 44
<211> LENGTH: 27
<212> TYPE: DNA
<213> ORGANISM: Artificial Sequence
<220> FEATURE:
<223> OTHER INFORMATION: Synthetic Construct

<400> SEQUENCE: 44
gccagaaagt ggacaaggtg tgaagag                                       27

<210> SEQ ID NO 45
<211> LENGTH: 27
<212> TYPE: DNA
<213> ORGANISM: Artificial Sequence
<220> FEATURE:
<223> OTHER INFORMATION: Synthetic Construct

<400> SEQUENCE: 45
gcagatttgc cagcttatat gactgtt                                       27

<210> SEQ ID NO 46
<211> LENGTH: 48
<212> TYPE: DNA
<213> ORGANISM: Artificial Sequence
<220> FEATURE:
<223> OTHER INFORMATION: Synthetic Construct

<400> SEQUENCE: 46
taatacgact cactataggg cataatatac aacaggatgg gggctgtg                48

<210> SEQ ID NO 47
<211> LENGTH: 49
<212> TYPE: DNA
<213> ORGANISM: Artificial Sequence
<220> FEATURE:
<223> OTHER INFORMATION: Synthetic Construct

<400> SEQUENCE: 47
taatacgact cactataggg gataatcatc atcccaggcg acaaagatg              49
```

<210> SEQ ID NO 48
<211> LENGTH: 52
<212> TYPE: DNA
<213> ORGANISM: Artificial Sequence
<220> FEATURE:
<223> OTHER INFORMATION: Synthetic Construct

<400> SEQUENCE: 48
taatacgact cactataggg tatatgatat gcctataaca aatgaccaga aa    52

<210> SEQ ID NO 49
<211> LENGTH: 51
<212> TYPE: DNA
<213> ORGANISM: Artificial Sequence
<220> FEATURE:
<223> OTHER INFORMATION: Synthetic Construct

<400> SEQUENCE: 49
taatacgact cactataggg actagccaga aagtggacaa ggtgtgaaga g    51

<210> SEQ ID NO 50
<211> LENGTH: 51
<212> TYPE: DNA
<213> ORGANISM: Artificial Sequence
<220> FEATURE:
<223> OTHER INFORMATION: Synthetic Construct

<400> SEQUENCE: 50
taatacgact cactataggg atcagcagat ttgccagctt atatgactgt t    51

<210> SEQ ID NO 51
<211> LENGTH: 42
<212> TYPE: DNA
<213> ORGANISM: Artificial Sequence
<220> FEATURE:
<223> OTHER INFORMATION: Synthetic Construct

<400> SEQUENCE: 51
caggaaacag ctatgaccat atacaacagg atgggggctg tg    42

<210> SEQ ID NO 52
<211> LENGTH: 43
<212> TYPE: DNA
<213> ORGANISM: Artificial Sequence
<220> FEATURE:
<223> OTHER INFORMATION: Synthetic Construct

<400> SEQUENCE: 52
caggaaacag ctatgaccat catcatccca ggcgacaaag atg    43

<210> SEQ ID NO 53
<211> LENGTH: 46
<212> TYPE: DNA
<213> ORGANISM: Artificial Sequence
<220> FEATURE:
<223> OTHER INFORMATION: Synthetic Construct

<400> SEQUENCE: 53
caggaaacag ctatgacctg atatgcctat aacaaatgac cagaaa    46

<210> SEQ ID NO 54
<211> LENGTH: 45
<212> TYPE: DNA
<213> ORGANISM: Artificial Sequence
<220> FEATURE:
<223> OTHER INFORMATION: Synthetic Construct

```
<400> SEQUENCE: 54
caggaaacag ctatgaccgc cagaaagtgg acaaggtgtg aagag                45

<210> SEQ ID NO 55
<211> LENGTH: 45
<212> TYPE: DNA
<213> ORGANISM: Artificial Sequence
<220> FEATURE:
<223> OTHER INFORMATION: Synthetic Construct

<400> SEQUENCE: 55
caggaaacag ctatgaccgc agatttgcca gcttatatga ctgtt                45
```

GENOTYPING METHOD

CROSS-REFERENCE TO RELATED APPLICATIONS

This application is filed under the provisions of 35 U.S.C. §121 and is a divisional of U.S. patent application Ser. No. 13/510,226, filed on Jul. 18, 2012 and entitled "GENOTYPING METHOD" in the name of Sung Whan AN, et al., which claims priority to International Patent Application No. PCT/KR2010/008055 filed on 15 Nov. 2010, which claims priority to Korean Patent Application No. 10-2009-0110331 filed 16 Nov. 2009, all of which are hereby incorporated by reference herein in their entirety.

TECHNICAL FIELD

The present invention relates to a genotyping method, and more particularly to an ID sequence, which is assigned to each genotype, and a multiplex genotyping method which uses the ID sequence.

BACKGROUND ART

Methods which have been developed for detecting infectious organisms include traditional methods of identifying the physical and chemical characteristics of pathogens by cultivation, and methods of detecting the specific genetic characteristics of pathogens. The methods for detecting genetic characteristics include restriction fragment length polymorphism (RFLP) analysis, amplified fragment length polymorphism (AFLP) analysis, pulsed-field gel electrophoresis, arbitrarily-primed polymerase chain reaction (AP-PCR), repetitive sequence-based PCR, ribotyping, and comparative nucleic acid sequencing. These methods are generally too slow, expensive, irreproducible, and technically demanding to be used in most diagnostic settings. All of the above-mentioned methods generally require that a cumbersome gel electrophoretic step be used, that the pathogen be grown in culture, that its genomic DNA be purified, and that the sample not contain more than one type of organism. These limitations also apply to recently developed detection methods which employ high density microarrays (Salazar et al., Nucleic Acids Res. 24:5056-5057, 1996; Troesch et al., J. Clin. Microbiol. 37:49-55, 1999; Lashkari et al., Proc. Natil. Acad. Sci. U.S.A. 94: 13057-13062, 1997). Meanwhile, pyrosequencing is a method of DNA sequencing based on the "sequencing by DNA synthesis" principle, which relies on the detection of pyrophosphate release on nucleotide incorporation, unlike the traditional Sanger sequencing method. In the pyrosequencing method, four deoxynucleotide triphosphates (dNTPs) are sequentially added one by one during polymerization. PPi attached to the dNTPs being polymerized emit light by enzymatic reactions, and the emitted light shows a signal peak according to the reaction order of each of the sequentially added dNTPs, in which the peak shows a pattern which is high or low in proportion to the number of the reacted dNTPs, such that the nucleotide sequence of the pathogen can be determined. In recent years, methods of detecting pathogenic bacteria or viruses in clinical samples based on pyrograms obtained by pyrosequencing of the PCR products of sequences specific to the pathogens have been used (Travasso, C M et al, *J. Biosci.*, 33:73-80, 2008; Gharizadeh, B et al., *Molecular and Cellular Probes,* 20, 230-238, 2006; Hoffmann, C et al., *Nucleic Acid Research,* 1-8, 2007).

In the pyrosequencing technique, however, nucleotide sequencing is performed according to the dispensation order of dNTPs, and a nucleotide in a template, which is absent in the dispensation order, does not react, and thus does not form a peak. However, when identical nucleotides in the dispensation order continuously appear, the heights of the peaks are determined according to the intensities of light emitted. Accordingly, when various pathogens exist in the same sample, the peaks of the nucleotides of the various pathogens appear overlapped, thus making it difficult to identify the genotypes through the interpretation of pyrograms. Particularly, as the number of repetitive sequences increases, the peaks of the anterior sequences become relatively lower. Thus, in the case of infection with multiple pathogens, it is difficult to detect a peak according to the degree of infection with each pathogen.

Accordingly, the present inventors have made extensive efforts to enable the genotypes of interest to be identified by unique and simple pyrograms obtained when performing genotyping using pyrosequencing. As a result, the present inventors have found that, when an ID sequence, which has an ID mark, a signpost and an endmark while existing independently of the specific sequence to be typed, is linked with the specific sequence and is used to perform pyrosequencing, a unique and simple pyrogram can be obtained for each genotype, thereby completing the present invention.

DISCLOSURE OF INVENTION

It is an object of the present invention to provide an ID sequence which is useful to perform pyrosequencing so as to enable the genotypes of interest to be identified by unique and simple pyrograms.

Another object of the present invention is to provide a genotyping method which ues said ID sequence.

Still another object of the present invention is to provide a method of genotyping HPV using said ID sequence.

Yet another object of the present invention is to provide a method of detecting KRAS gene mutation using said ID sequence.

A further object of the present invention is to provide a method of detecting respiratory virus using said ID sequence.

To achieve the above objects, the present invention provides an ID sequence for genotyping which consists of A(ID-S)n-E, wherein ID is an ID mark which is a single nucleotide selected from among A, T, C and G; S is a signpost which is a nucleotide linked with the adjacent ID mark and different from that of the adjacent ID mark; E is an endmark which is a nucleotide different from that of the signpost; and n is a natural number ranging from 1 to 32.

The present invention also provides an ID sequence for genotyping which consists of ID-S, wherein ID is an ID mark which is a nucleotide selected from among A, T, C and G, and S is a signpost which is a nucleotide linked with the adjacent ID mark and different from that of the adjacent ID mark.

The present invention also provides a genotyping primer comprising a gene-specific sequence for genotyping linked to said ID sequence.

The present invention also provides a genotyping method which comprises using said genotyping primer.

The present invention also provides a method for genotyping HPV, the method comprising the steps of: (a) designing an ID sequence for genotyping according to the genotype of each HPV virus, the ID sequence consisting of (ID-S)n-E, wherein ID is an ID mark which is a nucleotide selected from among A, T, C and G; S is a signpost which is a nucleotide linked with the adjacent ID mark and different from that of the adjacent ID mark; E is an endmark which is a nucleotide different from that of the signpost, and n is a natural number ranging from 1 to 32; (b) constructing a genotyping primer composed of a pyrosequencing primer sequence, the ID sequence, and a sequence specific to a virus genotype corresponding to the ID sequence; (c) amplifying an HPV virus-containing sample by PCR using the genotyping primer; and (d) subjecting the amplified PCR product to pyrosequencing to obtain a sequence for the ID sequence, and distinguishing the genotype of HPV according to the ID sequence.

The present invention also provides a method for detecting KRAS gene mutation, the method comprising the steps of: (a) designing an ID sequence for genotyping according to the gene mutation of each KRAS, the ID sequence consisting of (ID-S)n-E wherein ID is an ID mark which is a nucleotide selected from among A, T, C and G; S is a signpost which is a nucleotide linked with the adjacent ID mark and different from that of the adjacent ID mark; E is an endmark which is a nucleotide different from that of the signpost, and n is a natural number ranging from 1 to 32; (b) constructing a detection primer composed of a pyrosequencing primer sequence, the ID sequence, and a sequence specific for a KRAS gene mutation corresponding to the ID sequence; (c) amplifying a KRAS gene-containing sample by PCR using the detection primer; and (d) subjecting the amplified PCR product to pyrosequencing to obtain a pyrogram for the ID sequence, and detecting the KRAS gene mutation according to the ID sequence.

The present invention also provides a method for detecting respiratory virus, the method comprising the steps of: (a) designing an ID sequence for genotyping according to the genotype of each of influenza A virus, influenza B virus, RSV B, rhinovirus, and coronavirus OC43, the ID sequence consisting of (ID-S)n-E wherein ID is an ID mark which is a nucleotide selected from among A, T, C and G; S is a signpost which is a nucleotide linked with the adjacent ID mark and different from that of the adjacent ID mark, E is an endmark which is a nucleotide different from that of the signpost, and n is a natural number ranging from 1 to 32; (b) constructing a detection primer composed of a pyrosequencing primer sequence, the ID sequence, and a sequence specific to each respiratory virus gene corresponding to the ID sequence; (c) amplifying a sample, which contains a respiratory virus selected from the group consisting of influenza A virus, influenza B virus, RSV B, rhinovirus, and coronavirus OC43, by PCR using the detection primer; and (d) subjecting the amplified PCR product to pyrosequencing to obtain a pyrogram for the ID sequence, and detecting the respiratory virus according to the ID sequence.

BEST MODE FOR CARRYING OUT THE INVENTION

Other features and embodiments of the present invention will be more apparent from the following detailed descriptions and the appended claims In one aspect, the present invention is directed to an ID sequence for genotyping which consists of A(ID-S)n-E, wherein ID is an ID mark which is a nucleotide selected from among A, T, C and G; S is a signpost which is a nucleotide linked with the adjacent ID mark and different from that of the adjacent ID mark, E is an endmark which is a nucleotide different from that of the signpost; and n is a natural number ranging from 1 to 32.

In another aspect, the present invention is directed to an ID sequence for genotyping which consists of ID-S, wherein ID is an ID mark which is a nucleotide selected from among A, T, C and G, and S is a signpost which is a nucleotide linked with the adjacent ID mark and different from that of the adjacent ID mark.

As used herein, the term "ID sequence" is not a specific sequence conserved in each gene and refers to an artificially constructed nucleotide sequence which can be specifically assigned to each genotype in the genotyping method of the present invention.

As used herein, the term "adjacent ID mark" means an ID mark located ahead of or behind the signpost.

The ID sequence of the present invention is used to perform pyrosequencing such that the pyrogram is distinguished by one nucleotide according to the determined dispensation order using the signpost and the endmark, which allow the pyrogram peak to be formed at a specific location without being influenced by the next sequence.

In this invention, a nucleotide that forms a specific peak according to the dispensation order in this pyrosequencing process is named "ID mark", and a sequence comprising the signpost and the endmark, which is a sequence required for forming a single peak by the ID mark, is named "ID sequence". There can be three types of ID marks which are not influenced by a gene sequence located next to the ID mark through the use of one signpost and one endmark, and thus the number of types that can be genotyped is three. In order to perform multiplex genotyping of more than three types, additional signposts and ID marks are required.

Figure 1:
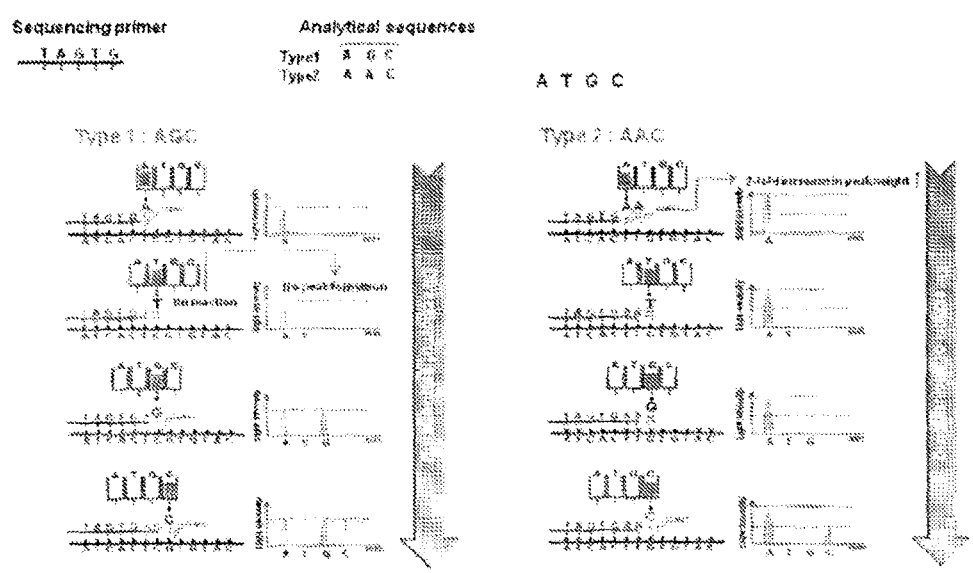
FIG. 1 shows a pyrosequencing process, which is performed according a dispensation order, and the resulting pyrogram.

In general pyrosequencing, nucleotide sequencing is performed according to the dispensation order (the order of nucleotide addition in DNA synthesis), and if a template has a nucleotide absent in the dispensation order, no reaction will occur, and thus no peak will be formed, but if a sequence identical to the sequence included in the dispensation order is continuously present in the template, the height of the peak is formed according to the intensity of light emitted (FIG. 1).

Figure 2:
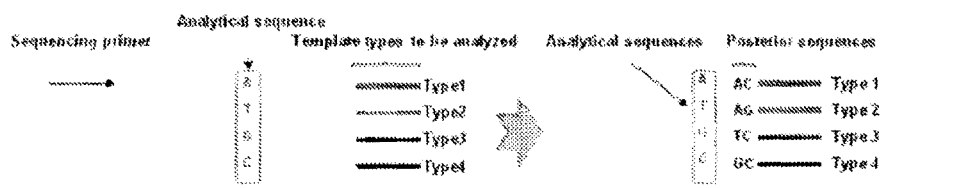
FIG. 2 shows the change in pyrogram peaks according to analytical sequences.
Figure 2:
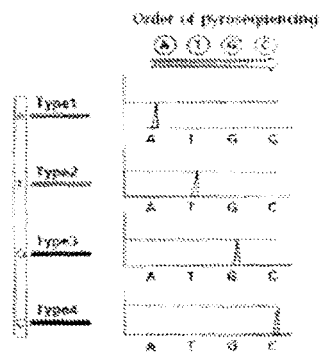
Figure 2:
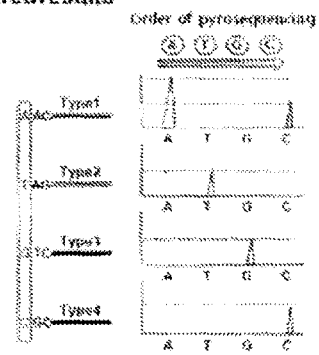

It is believed that, when one nucleotide is used as an analytical sequence, it can be distinguished by four different peaks on the pyrogram. However, in fact, a sequence next to the analytical sequence is one of A, T, G and C, and thus in at least one case, multiple peaks (if the identical sequences are repeated, one large peak is formed) are necessarily formed. As a result, there are at most three methods capable of distinguishing a single peak by a single nucleotide (FIG. 2).

Figure 3:
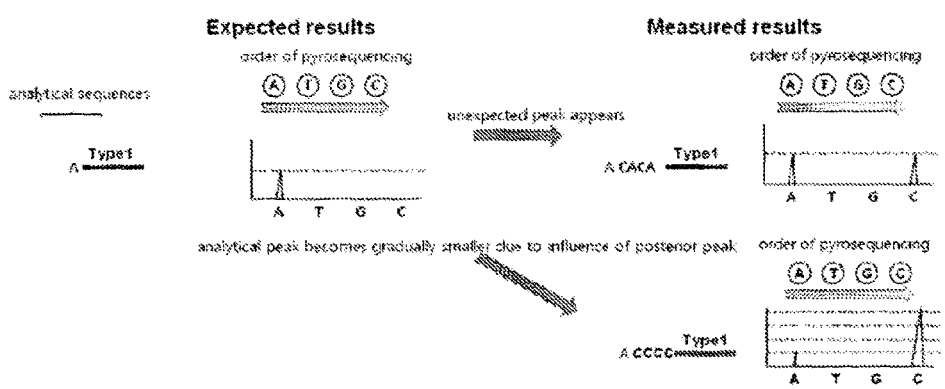
FIG. 3 shows the change in pyrogram peaks according to analytical sequences.

In addition, an undesired peak is formed due to a sequence following the analytical sequence, and if repeated nucleotides are continuously present following the analysis sequence, polymerization reactions will occur at once to form a single peak. However, because the intensity of light generated in the reactions increases, the height of the peak proportionally increases, and if such repetitive sequences exist, the height of the peak for a single nucleotide relatively decreases (FIG. 3). Because of such problems, there is a limit to multiplex genotyping which uses a single nucleotide. To solve such problems, in the ID sequence of the present invention, a sequence that separates the "analytical sequence" so as not to be influenced by the next sequence and allows additional analysis is named "signpost" (FIG. 4).

In addition, a design of the dispensation order for pyrosequencing varies depending on the signpost sequence.

Figure 4:
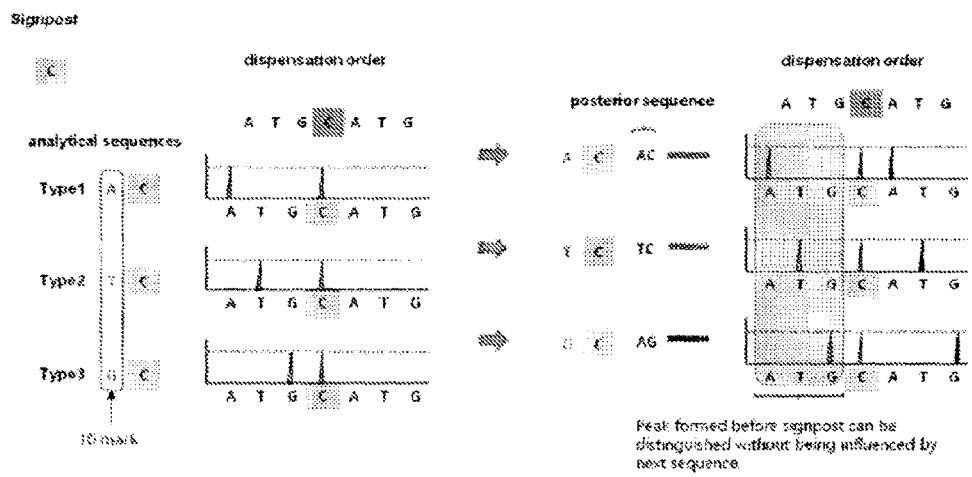
FIG. 4 shows the change in pyrogram peaks, which results from insertion of a signpost.

If one nucleotide in an analytical sequence consisting of two nucleotides is set as a signpost, each of three nucleotides can be located at the site of the remaining one nucleotide (if identical sequences are located, the peaks will overlap, and thus three nucleotides excluding the nucleotide assigned as the signpost can be located at the remaining one nucleotide site), and the nucleotide located ahead of the signpost can be set as shown in FIG. 4 such that the peak can be independently distinguished without being influenced by the nucleotide located behind the analytical sequence.

The single nucleotide separated by the signpost in the analytical sequence is named "ID mark", and as shown in FIG. 4, multiplex genotyping of three types is possible using one ID mark and one signpost. Herein, the position of the signpost in the dispensation order is after the ID mark (because only the ID mark located ahead of the signpost is not influenced by the sequence located following the analytical sequence).

Figure 5:
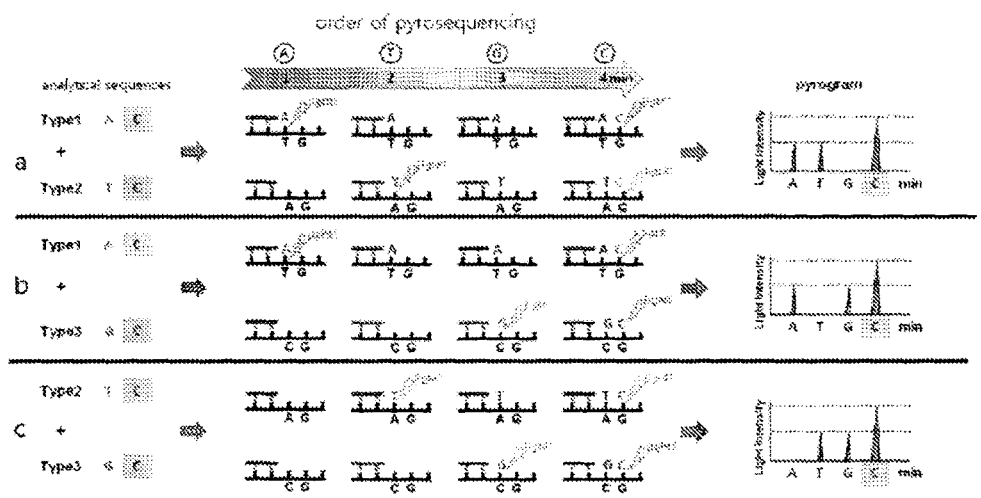
FIG. 5 shows pyrograms obtained for a mixture of two different analytical sequences.

In one aspect of the present invention, in order to genotype a two-nucleotide analytical sequence consisting of a one-nucleotide ID mark and a signpost, as shown in FIG. 5, analytical sequences of type 1 (analytical sequence: AC), type 2 (analytical sequence: TC) and type 3 (analytical sequence: GC) are synthesized and subjected to pyrosequencing. As a result, for type 1, the peak of A appears in dispensation order 1, and the peak of C appears in dispensation order 4. For type 2, the peak of T appears in dispensation order 2, and the peak of C appears in dispensation order 4. For type 3, the peak of G appears in dispensation order 3, and the peak of C appears in dispensation order 4. Herein, A, T and G which are the first nucleotides of the analytical sequences are respectively ID marks, and C which is the second nucleotide of each of the analytical sequences is a signpost.

To perform multiplex genotyping for the three types of analytical sequences, as shown in FIG. 5(a), a sample consisting of type 1 (analytical sequence: AC) and type 2 (analytical sequence: TC) is pyrosequenced in the dispensation order of A→T→G→C. As a result, the peak of A appears in dispensation sequence 1, the peak of T appears in dispensation sequence 2, no peak appears in dispensation sequence 3, and the peak of C that is the signpost appears in dispensation sequence 4. Herein, the peak of the signpost C is two times higher than the peaks of A and T and present in both the two types, and thus the amount of the reaction is two times larger and the peak intensity is also two times higher than those of A and T.

Similarly, as shown in FIG. 5(b), in the case of a sample consisting of type 1 (analytical sequence: AC) and type 3 (analytical sequence: GC), the peak of A appears in dispensation order 1, the peak of G appears in dispensation order 3, no peak appears in dispensation order 2, and the peak of C that is the signpost appears in dispensation order 4. Herein, the peak of the signpost C is two times higher and present in both the two types, and thus the amount of the reaction is two times larger and the peak intensity is also two times higher.

In addition, as shown in FIG. 5(c), in the case of a sample consisting of type 2 (analytical sequence: TC) and type 3 (analytical sequence: GC), the peak of T appears in dispensation order 2, the peak of G appears in dispensation order 3, no peak appeared in dispensation order 1, and the peak of C that is the signpost appears in dispensation order 4. Herein, the peak of the signpost C is two times higher and is present in both the two types, and thus the amount of the reaction is two times larger and the peak intensity is also two times higher.

Accordingly, the ID mark can be separated from the next sequence by the signpost and can be present independently of the next sequence. Thus, it can advantageously be used in multiplex genotyping.

Figure 6:
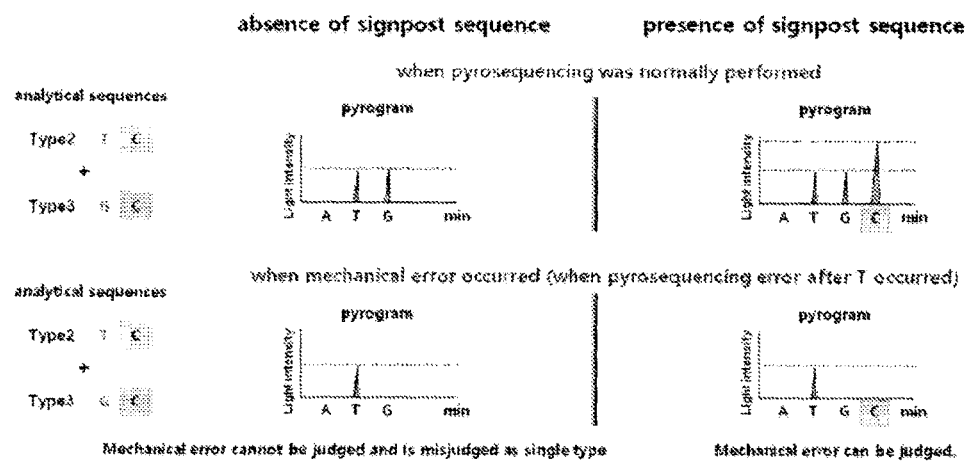
FIG. 6 shows pyrograms obtained in the presence or absence of a signpost in a dispensation order.

The results of genotyping in pyrosequencing performed using an analytical sequence consisting of an "ID mark" and a "signpost" are not influenced by whether or not the sequence of the signpost is inserted into the dispensation order. However, if the sequence of the signpost is not inserted into the dispensation order, there will be a problem in that a mechanical error cannot be judged (FIG. 6). For this reason, the sequence of the signpost is preferably inserted into the dispensation order to make it possible to determine whether or not pyrosequencing was normally performed. In addition, because the peak of the ID mark in multiplex genotyping in pyrosequencing isn't able to be higher than the peak of the signpost, this can also be used as a reference for judging pyrosequencing error (FIG. 6).

Endmark

Figure 7:
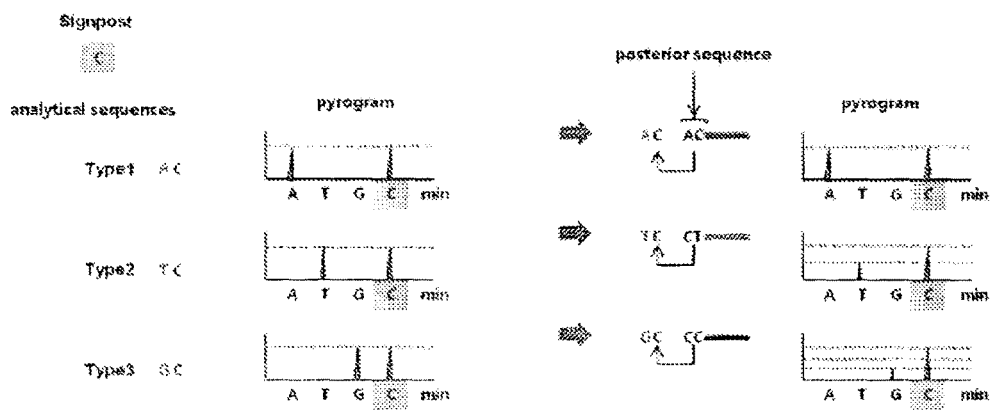
FIG. 7 shows the changes in pyrogram patterns according to the changes in a sequence posterior to a signpost.

The signpost functions to separate the single-nucleotide ID mark from the next sequence so as not to be influenced by the next sequence. However, when the next sequence is identical to the signpost, the height of the peak increases in proportion to the increase in the intensity of light emitted. For this reason, there can occur a phenomenon that the height of the peak of the ID mark changes (FIG. 7). To solve this phenomenon, a nucleotide sequence different from the signpost can be inserted following the signpost in order to prevent the ID mark and the signpost from being influenced by the next sequence. Herein, the inserted sequence is named "endmark", and the endmark is not inserted in the dispensation order. The endmark functions to prevent the ID mark and the signpost from being influenced by the next sequence and make the peak height constant.

Figure 8:
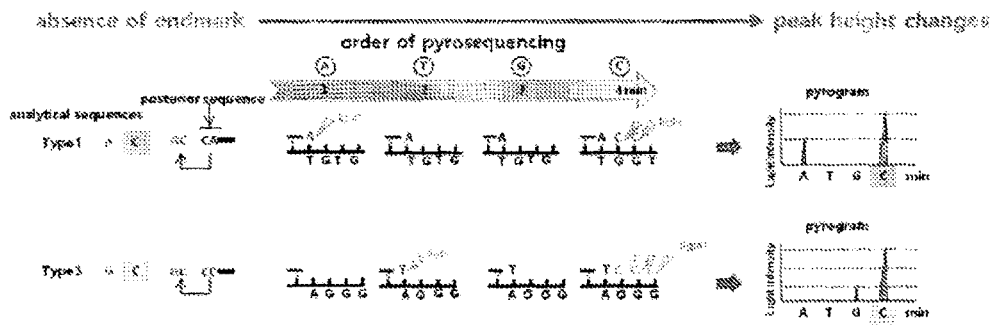
FIG. 8 shows pyrograms obtained in the absence of an endmark.

In order words, in the case in which the endmark is absent as shown in FIG. 8, if type 1 (analytical sequence: AC) is followed by CA and if pyrosequencing is performed in the dispensation order of A→T→G→C, the peak of C in dispensation order 3 will be larger than the peak of A in dispensation order 1, because of the overlapping C next to the signpost C. Similarly, if type 3 (analytical sequence: GC) is followed by CC, the peak of G in dispensation order 3 will be much smaller than the excessively large peak of C in dispensation order 4, because C next to the signpost C overlaps three times.

Figure 9:
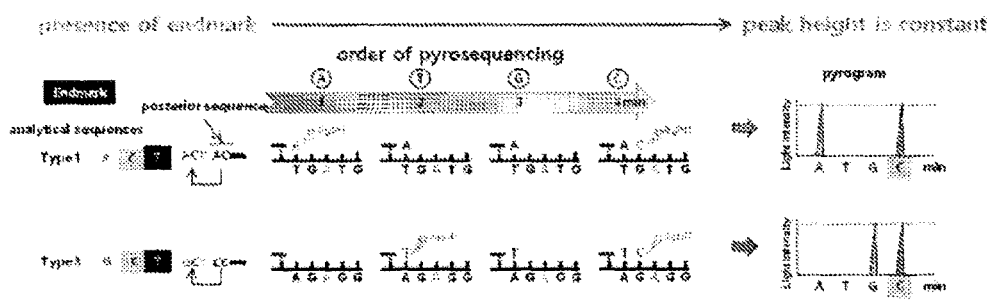
FIG. 9 shows pyrograms obtained in the presence of an endmark.

In the case in which the endmark is present as shown in FIG. 9, if type 1 (analytical sequence: AC) is followed by CA and if T as the endmark is inserted therebetween and if pyrosequencing is performed in the dispensation order of A→T→G→C, C will not overlap due to the insertion of T next to the signpost C, and the height of the peak of A in dispensation order 1 and the height of the peak of C in dispensation order 3 will be constant. Similarly, if type 3 (analytical sequence: GC) is followed by CC, C next to the signpost will not overlap due to the insertion of the endmark T next to the signpost C, and the height of the peak of G in dispensation order 3 will be equal to the height of the peak of C in dispensation order 4. In the present invention, the number N of signposts that can be added is preferably 2-32, and if N is 32, genotyping of 65 types is possible.

Figure 27:
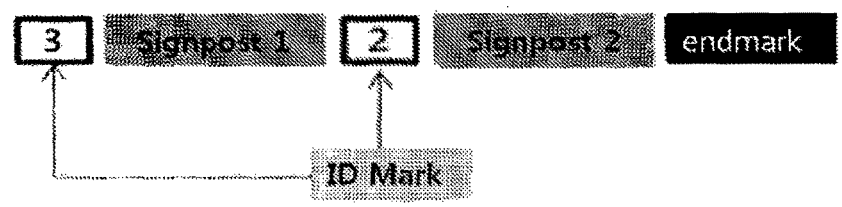
FIG. 27 shows a sequence including a plurality of ID marks and a plurality of signposts.

When a plurality of ID marks and a plurality of signposts are used, genotyping of 3 or more types is possible (see FIG. 27).

In this case, the adjacent nucleotide sequences should differ from each other in order to obtain pyrograms of single peaks. The ID mark can be located ahead of the signpost or between two signposts. The ID mark located between two signposts may consist of two different nucleotides, because it must have nucleotides different from the signposts located at both sides thereof. In addition, the ID mark located ahead of the signpost may consist of three different nucleotides, because it must have a nucleotide different from the signpost located behind thereof.

Figure 28:
FIG. 28 shows another sequence including a plurality of ID marks and a plurality of signposts.

Herein, the nucleotide of signpost 1 should not be identical to the nucleotide of signpost 3, and the nucleotide sequence of the most posterior signpost must also not be identical to the base sequence of the endmark (see FIG. 28).

In the present invention, the sequence consisting of the ID mark, the signpost and the endmark is named "ID sequence". In the present invention, the ID sequence may also be composed of the ID mark and the signpost. Preferably, it consists of the ID mark, the signpost and the endmark.

Whenever one signpost is added, the ID sequence of the present invention enables two additional types to be distinguished. Thus, it enables 2N+1 (N=the number of signposts) types to be distinguished by genotyping according to the location of the ID mark.

Figure 10:
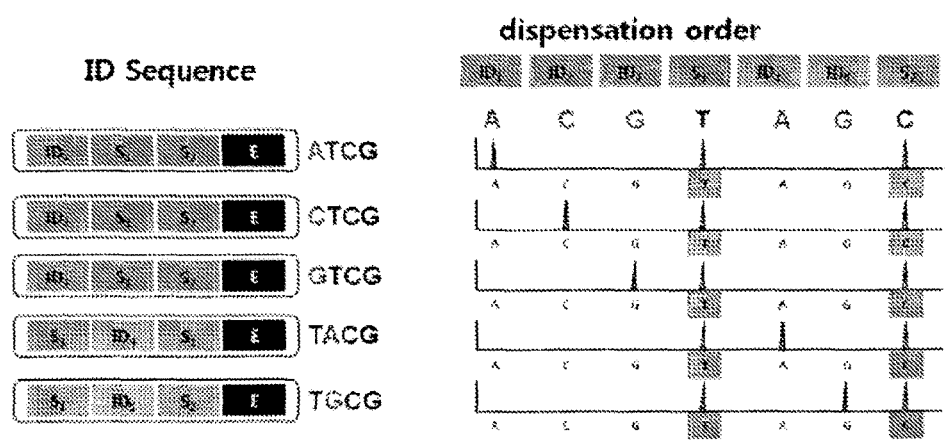
FIG. 10 shows the change in the dispensation order according to the change in the order of a signpost.
Figure 10:
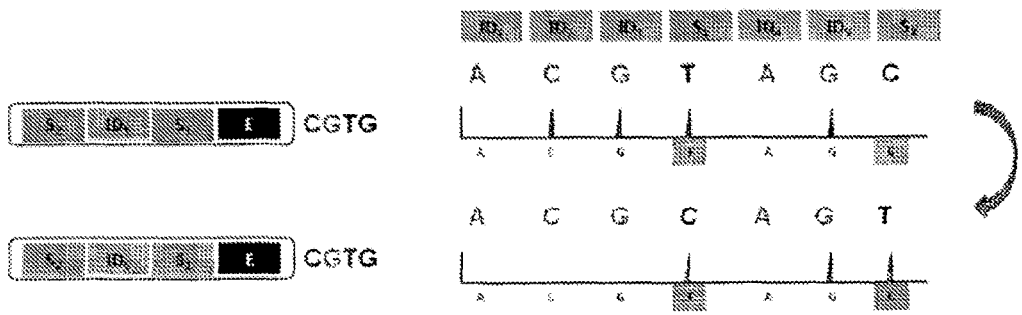

Nucleotide sequences excluding the ID mark and the endmark are used as the signposts. In order to distinguish the ID marks of the ID sequence in the same dispensation order, the nucleotide sequences of the signposts in the ID sequence must be located in the same order. In other words, only the ID mark should be located ahead of or between the signposts, and the signposts should be arranged in the same order. This is because, when the arrangement of the signposts changes, the dispensation order also changes due to the feature of pyrosequencing (FIG. 10).

Design of ID Sequence

Case of Making ID Sequence after Determining Signposts

Figure 29:
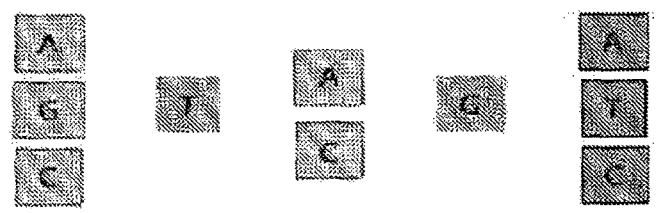
FIG. 29 shows a sequence including an ID mark which may be any one of A, G and C, a first signpost T, and ID mark which may be A or C, a second signpost G, and an end mark which may be any one of A, T, and C.

In the case in which an ID sequence comprises two signposts, if T and G are used as signpost 1 and signpost 2, respectively, an ID mark which is located ahead of signpost 1 (T) may be any one of A, G and C, an ID mark which is located between signpost 1 and signpost 2 may be A or C, and an endmark may be any one of A, T and C (see FIG. 29).

Figure 11:
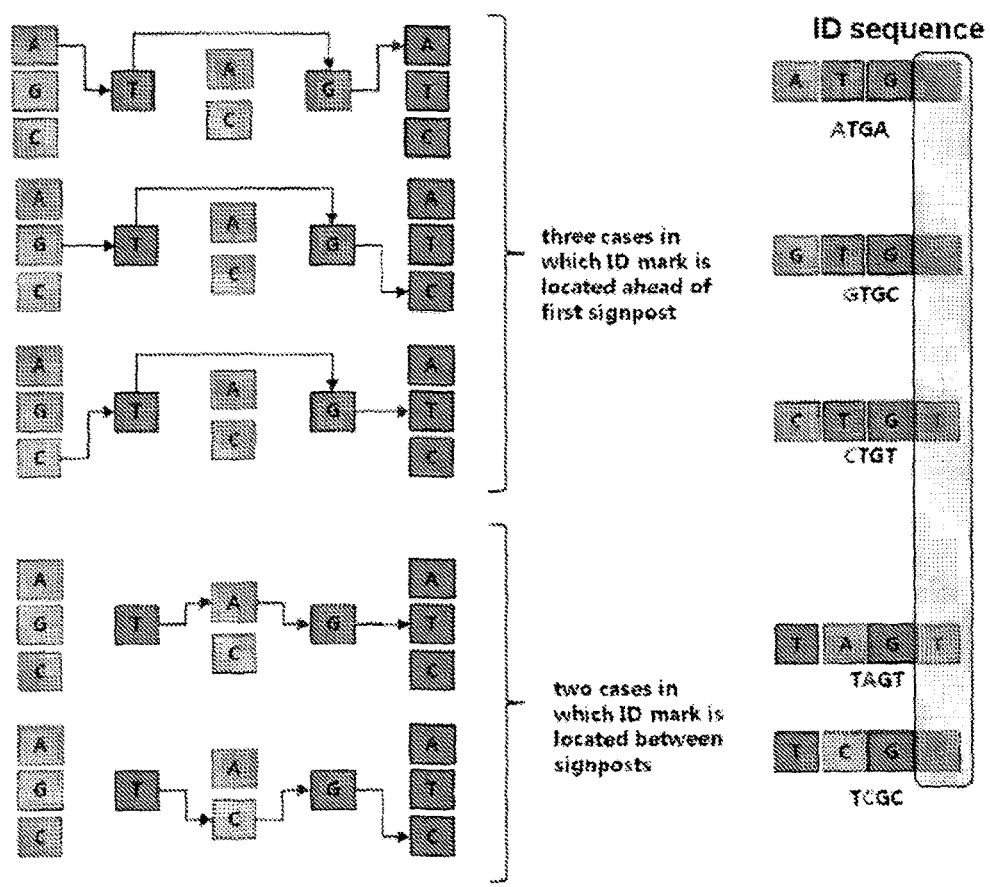
FIG. 11 shows a method of designing an ID sequence according to a dispensation order.

Thus, as shown in FIG. 11, there are the following five cases in which the ID sequence consisting of the ID mark, the signpost and the endmark can be produced using one ID mark: three cases (A, G and C) in which the ID mark is located ahead of signpost 1; and two cases (A and C) in which the ID mark is located between signpost 1 and signpost 2.

Herein, because the endmarks are not included in the dispensation order, the endmarks in the ID sequences may be the same or different.

Design of Dispensation Order

In genotyping which is performed using the ID sequence, the ID marks located in the ID sequence sequentially form independent peaks according to the dispensation order. The dispensation order can be designed according to various permutations which can be formed using the signpost as a boundary.

Figure 30:
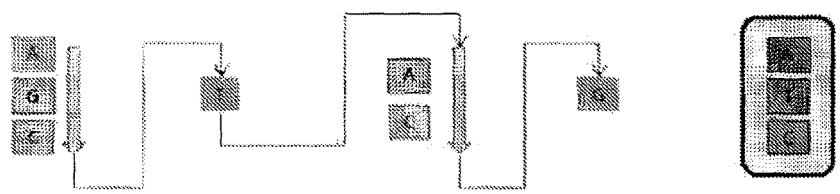
FIG. 30 shows a dispensation order for the sequence of FIG. 29, in which the end mark id not included.

One of dispensation orders which can be formed according to the ID sequence is shown in the following figure, and the endmark is not included in the dispensation order (see FIG. 30).

Figure 12:
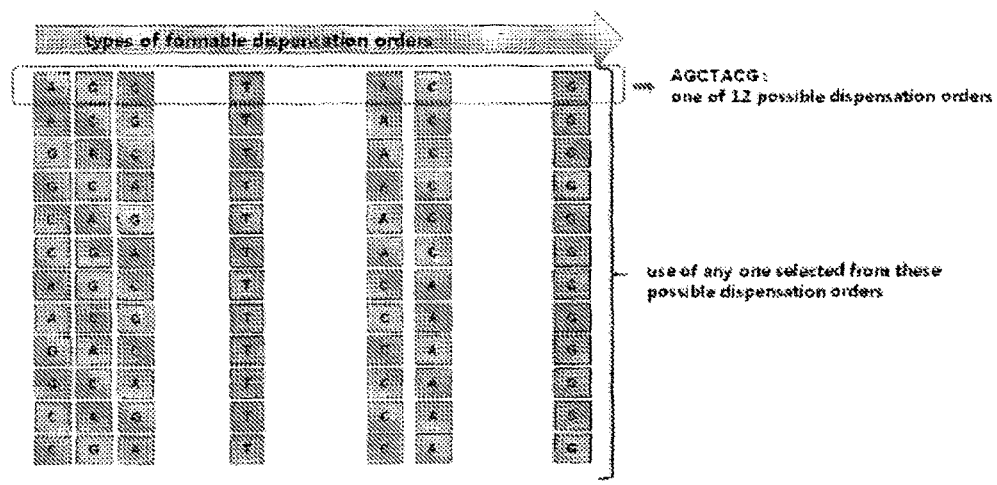
FIG. 12 shows a method of designing a dispensation order.

FIG. 12 shows 12 dispensation orders which can be formed according to the ID sequence, and one selected from among the 12 dispensation orders may be used.

Figure 31:
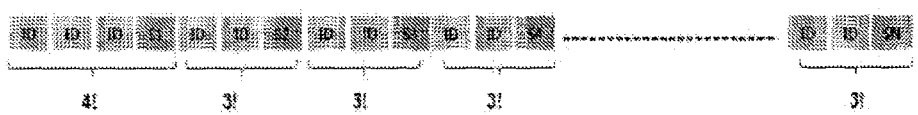
FIG. 31 shows a sequence of ID marks and signposts, associated with a number of dispensations orders.

The number of dispensation orders that can be formed is 4×6N (N=number of signposts). Thus, if the number of signposts is 2, then 144 dispensation orders may be made (see FIG. 31).

Figure 13:
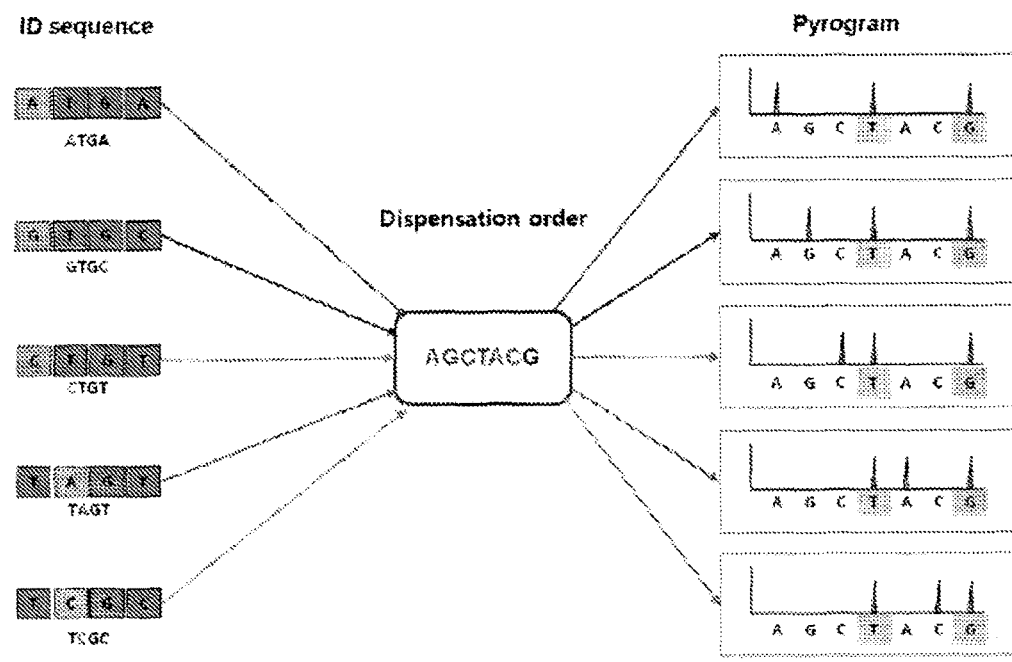
FIG. 13 shows pyrograms obtained by ID sequences according to dispensation orders.

Accordingly, as shown in FIG. 13, the ID sequence has characteristic peaks according to the dispensation order.

Method of Designing ID Sequence after Determining Dispensation Order

An ID sequence consists of one ID mark, one or more signposts and at least one endmark. In the ID sequence, the adjacent nucleotides must differ from each other, and the dispensation order must have the same conditions as described above. In addition, the ID sequence may also be designed after determining the dispensation order.

Figure 14:
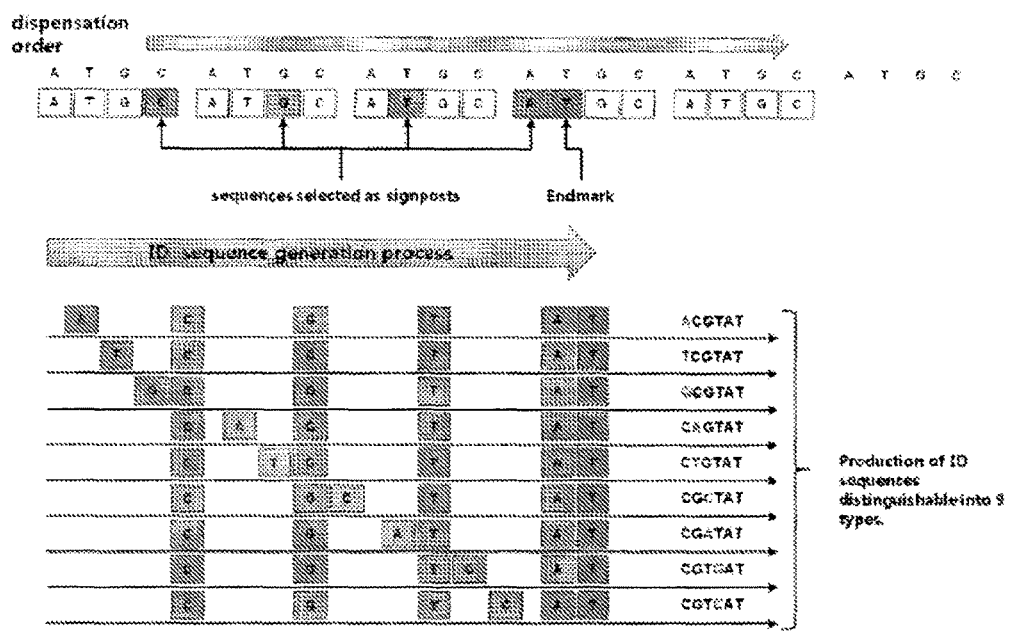
FIG. 14 shows a method of designing an ID sequence after determining a dispensation order.
Figure 15:
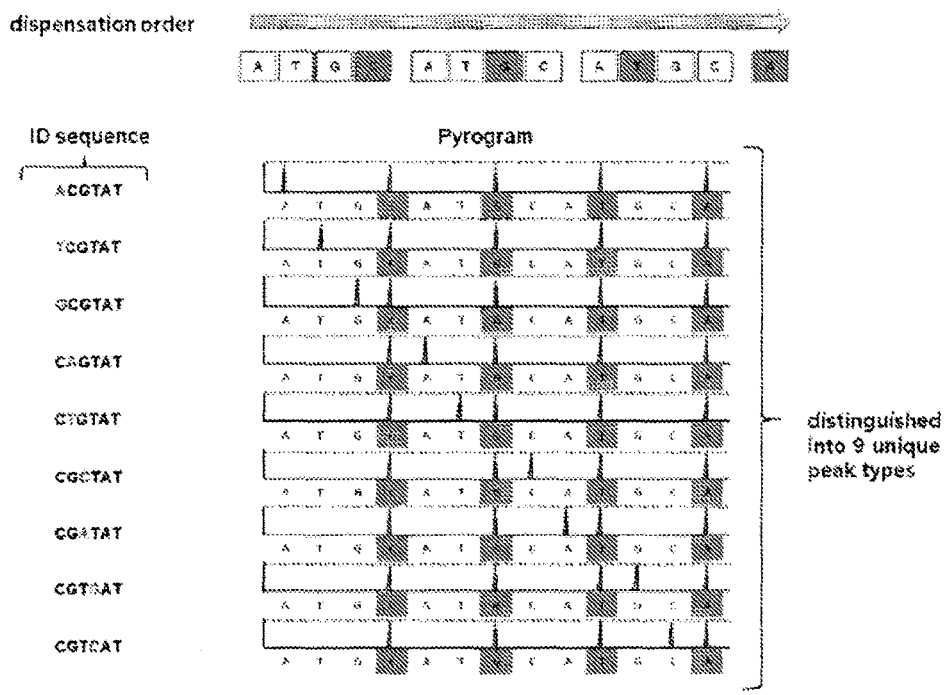
FIG. 15 shows pyrograms obtained by ID sequences according to dispensation orders.

In the dispensation order, three ID marks may be located ahead of signpost 1, and two ID marks may be located between two signposts. When this rule is used, the following ID sequence can be made with the dispensation order. For example, when 9 genotypes are to be separated, 4 signposts are required according to the formula (2N+1). As shown in FIG. 14, if the dispensation order is determined such that A, T, G and C are repeated n times, the signposts will be C, G, T and A, the endmark will be T, and the ID marks will be located between the signposts, thereby constructing an ID sequence. When pyrosequencing is performed according to the dispensation order, the results shown in FIG. 15 can be obtained.

In still another aspect, the present invention is directed to a genotyping primer comprising a gene-specific sequence for genotyping linked to said ID sequence.

In the present invention, the gene-specific sequence for genotyping is preferably a sequence specific to a gene selected from the group consisting of viral genes, disease genes, bacterial genes, and identification genes. The primer preferably additionally contains a sequencing primer sequence at the 5' terminal end in order to facilitate pyrosequencing.

In yet another aspect, the present invention is directed to a genotyping method which comprises using said genotyping primer.

The genotyping primer comprising the ID sequence of the present invention may be used in various genotyping methods which are performed using dispensation orders and sequencing methods. Preferably, it may be used in pyrosequencing methods and semiconductor sequencing methods, but is not limited thereto.

In the present invention, the pyrosequencing method is a method in which light emitted from the degradation of ppi (pyrophosphate) generated in a sequencing process, and the semiconductor sequencing method is a method in which the change in current by a proton ($H^+$ ion) generated in a sequencing process is analyzed by a chip (Andersona, Erik P. et al., Sens Actuators B Chem.; 129(1): 79, 2008).

The genotyping method of the present invention may comprise the steps of: (a) designing an ID sequence for genotyping according to the genotyping target gene, the ID sequence consisting of (ID-S)n-E, wherein ID is an ID mark which is a nucleotide selected from among A, T, C and G, S is a signpost which is a nucleotide linked with the adjacent ID mark and different from that of the adjacent ID mark, E is an endmark which is a nucleotide different from that of the signpost, and n is a natural number ranging from 1 to 32; (b) amplifying the template of the genotyping target gene by PCR using a genotyping primer comprising a gene-specific sequence for genotyping linked to the designed ID sequence, thereby obtaining a PCR product; and (c) pyrosequencing the PCR product to obtain a pyrogram for the ID sequence.

In a further aspect, the present invention is directed to a method for genotyping HPV, the method comprising the steps of: (a) designing an ID sequence for genotyping according to the genotype of each HPV virus, the ID sequence consisting of (ID-S)n-E, wherein ID is an ID mark which is a nucleotide selected from among A, T, C and G; S is a signpost which is a nucleotide linked with the adjacent ID mark and different from that of the adjacent ID mark, E is an endmark which is a nucleotide different from that of the signpost, and n is a natural number ranging from 1 to 32; (b) constructing a genotyping primer composed of a pyrosequencing primer sequence, the ID sequence, and a sequence specific to a virus genotype corresponding to the ID sequence; (c) amplifying an HPV virus-containing sample by PCR using the genotyping primer; and (d) subjecting the amplified PCR product to pyrosequencing to obtain a pyrogram for the ID sequence, and distinguishing the genotype of HPV according to the ID sequence.

In the present invention, the sequence specific to a virus genotype may be selected among nucleotide sequences shown by SEQ ID NOS: 1 to 15.

HPV (human papilloma virus) is one of the most common viruses which infect the human skin or mucous membrane. Today more than about 150 HPV types are known, and about 30 kinds infect the genital tract. About 85% of cancers caused by HPV virus are associated with cervical cancer. Among 30 HPV types that infect the genital tract, 15 types are known as high-risk types that cause cervical cancer. Cervical cancer ranks sixth in cancer incidence among women in Korea, and Pap smears have poor sensitivity and reproducibility, and thus have problems involved in detecting precancerous conditions. In addition, these testing methods incur high cost due to frequent testing. HPV testing methods approved by the FDA to date include HybridCaptureII, but this method can diagnose only HPV infection and cannot determine what type of HPV infection is present.

Because HPV shows different cancer incidences, cancer types and cancer metastatic processes depending on the genotypes, it is important to identify the genotype of HPV, which infected the patient, by genotyping. For example, it was reported that 55% of the incidence of CIN III+ is associated with HPV type 16, 15% with HPV type 18, and the remaining 30% with HPV type 13.

The most important reason for genotyping HPV is that the genotyping makes it possible to monitor genotype-specific HPV infections. A period of persistent infection in older women generally is generally longer than that in younger women, and this is because the older women were highly likely to be infected for a long time. Although a critical period of persistent infection has not yet been clinically determined, it is generally known that an infection period longer than 1 year has increased risk. Although it is also important to identify HPV type 16 and HPV type 18, it is most important to examine persistent infection with carcinogenic HPV infection.

Figure 16:
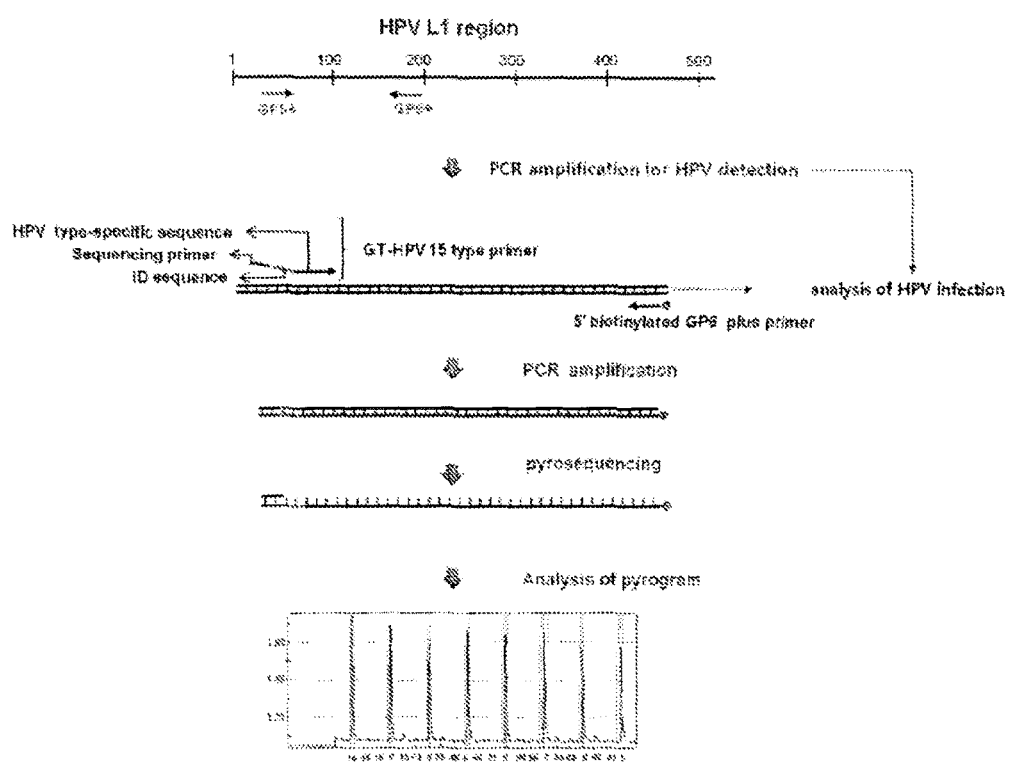
FIG. 16 shows a method of genotyping HPV using an ID sequence of the present invention.

In one example of the present invention, 15 HPV virus types were genotyped using the ID sequence. Each of 15 HPV viral genomes was amplified by PCR using HPV L1 protein specific to 15 HPV virus types, primers (GT-HPV 15type primer) containing 15 kinds of ID sequences and sequencing primer sequences, and a 5' biotinylated GP6 plus primer, and the PCR products were pyrosequenced. As a result, pyrograms of 15 ID sequences for 15 virus types could be obtained (FIG. 16).

In another example of the present invention, a sample of a mixture of the genome DNA of the CaSki cell line infected with HPV type 16 and the same amount of the genomic DNA of the HeLa cell line infected with HPV type 18 was amplified by PCR using a GT-HPV 15 type primer and a 5' biotinylated GP6 plus primer, and the PCR product was pyrosequenced. As a result, pyrograms of ID sequences, which were clear without the interference of overlapping peaks and corresponded to HPV type 16 and HPV type 18, could be obtained.

In a still further aspect, the present invention is directed to a method for detecting KRAS gene mutation, the method comprising the steps of: (a) designing an ID sequence for genotyping according to the gene mutation of each KRAS, the ID sequence consisting of (ID-S)n-E wherein ID is an ID mark which is a nucleotide selected from among A, T, C and G; S is a signpost which is a nucleotide linked with the adjacent ID mark and different from that of the adjacent ID mark, E is an endmark which is a nucleotide different from that of the signpost, and n is a natural number ranging from 1 to 32; (b) constructing a detection primer composed of a pyrosequencing primer sequence, the ID sequence, and a sequence specific for a KRAS gene mutation corresponding to the ID sequence; (c) amplifying a KRAS gene-containing sample by PCR using the detection primer; and (d) subjecting the amplified PCR product to pyrosequencing to obtain a pyrogram for the ID sequence, and detecting the KRAS gene mutation according to the ID sequence.

The Ras gene was first identified as a retroviral oncogene causing a sarcoma in rats. Since the presence of K-ras in the lymph node of pancreatic cancer patients was identified in 1985, various studies on the K-ras gene have been conducted. The mutation of this oncogene is frequently found in the malignant mutations of the human body. As genes having a structure and function similar to those of this oncogene, H-ras and N-ras are also known as oncogenes. Mutations in codons 12, 13 and 61 of K-ras influence the protein activity to cause excessive activity.

Mutations in the K-ras gene are found in adenocarcinoma of the digestive system. In the case of adenocarcinoma of the pancreas, 90% of mutations can be found in pancreatic juice and tissue and are known as mutations of codon 12. In addition, these mutations are found in 40-45% of colorectal cancer and are known to be associated with a decrease in the response to drugs such as cetuximab or panitumumab, which are used for progressed colon cancer that does not respond to chemotherapy. Furthermore, these mutations are observed in 5-30% of non-small cell lung and are observed mainly in smoking patients. In addition, these mutations are found exclusively with EGFR mutations.

Figure 17:
FIG. 17 shows a general system for detecting KRAS mutations.
Figure 17:
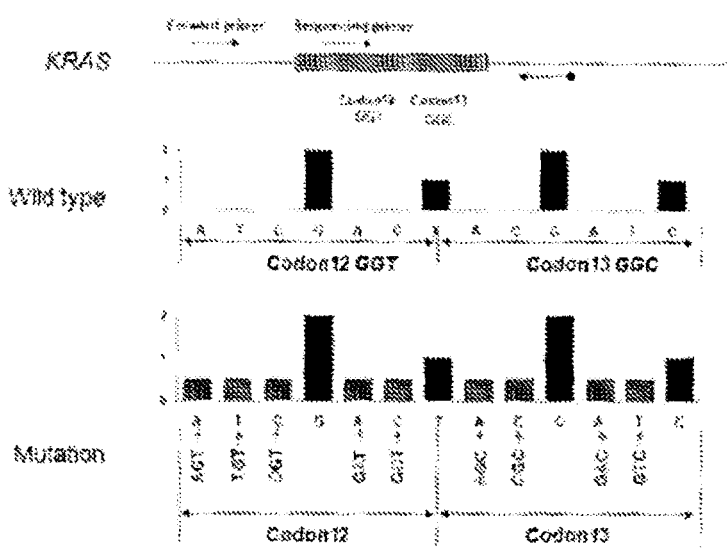
Figure 17:
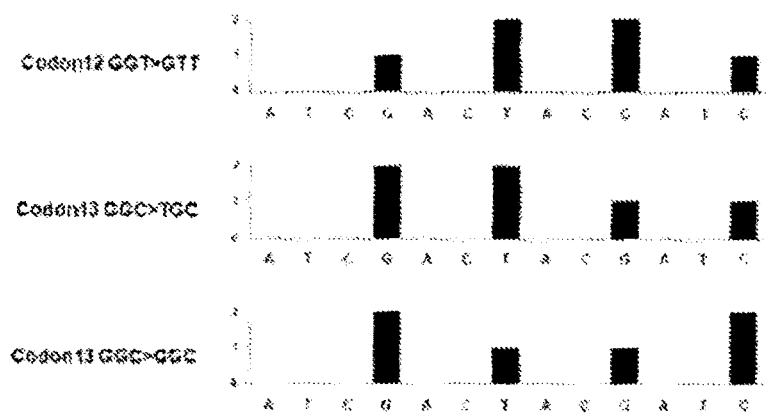

Three mutation types, including a mutation of codon 12 (GGT>GTT) and mutations of codon13 (GGC>TGC and GGC>GCC), in wild-type KRAS, are difficult to detect by a general pyrosequencing method. Particularly, the mutation of codon (GGT>GTT) has a high frequency of occurrence, and thus is difficult to exclude because of the detection limit (FIG. 17).

Figure 18:
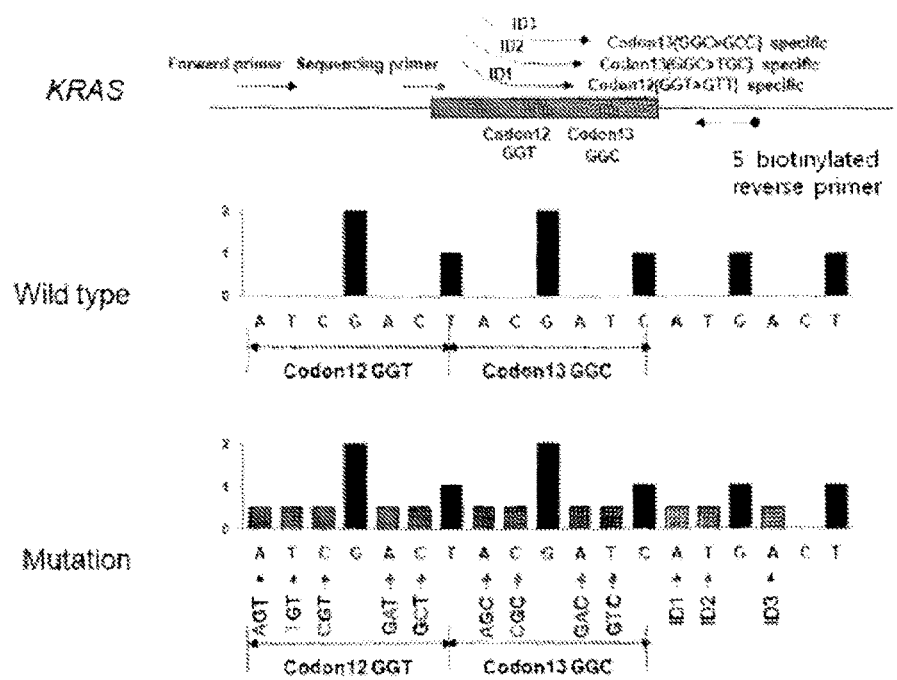
FIG. 18 shows a method of detecting KRAS mutations using ID sequences of the present invention.

In one example of the present invention, a method of detecting mutations in codon 12 and codon 13 of the KRAS gene was disclosed. In the present invention, primers binding specifically to the three types of mutations of codon 12 (GGT>GTT) and codon 13 (GGC>TGC and GGC>GCC) were designed such that the mutations can be detected using ID sequences located ahead of nucleotide sequences specific to the three types of primers. According to the method of the present invention, 12 types of KRAS mutations can be detected by a single PCR process using 3 types of forward primers and 1 type of biotinylated reverse primer (FIG. 18).

In the present invention, the sequence specific for a KRAS gene mutation may be selected among nucleotide sequences shown by SEQ ID NOS: 34 to 35.

In a yet further aspect, the present invention is directed to a method for detecting respiratory virus, the method comprising the steps of: (a) designing an ID sequence for genotyping according to the genotype of each of influenza A virus, influenza B virus, RSV B, rhinovirus, and coronavirus OC43, the ID sequence consisting of (ID-S)n-E wherein ID is an ID mark which is a nucleotide selected from among A, T, C and G; S is a signpost which is a nucleotide linked with the adjacent ID mark and different from that of the adjacent ID mark, E is an endmark which is a nucleotide different from that of the signpost, and n is a natural number ranging from 1 to 32; (b) constructing a detection primer composed of a pyrosequencing primer sequence, the ID sequence, and a sequence specific to each respiratory virus gene corresponding to the ID sequence; (c) amplifying a sample, which contains a respiratory virus selected from the group consisting of influenza A virus, influenza B virus, RSV B, rhinovirus, and coronavirus OC43, by PCR using the detection primer; and (d) subjecting the amplified PCR product to pyrosequencing to obtain a pyrogram for the ID sequence, and detecting the respiratory virus according to the ID sequence.

In one example of the present invention, a method of detecting respiratory virus was disclosed. In this method, primers binding specifically to 5 types of respiratory viruses are designed such that the viruses can be detected using ID sequences located ahead of nucleotide sequences specific to the primers. cDNA is synthesized using 5 types of forward primers binding to 5 types of GT-respiratory viruses and 1 type of biotinylated reverse primer, and was amplified by PCR using a GT-RespiVirus ID primer and a 5'-biotinylated M13 reverse primer, and the PCR products were pyrosequenced.

In the present invention, the sequences specific to the respiratory virus genotypes may be nucleotide sequences shown by SEQ ID NO: 41 for influenza A virus, SEQ ID NO: 42 for influenza B virus, SEQ ID NO: 43 for RSV B, SEQ ID NO: 44 for rhinovirus, and SEQ ID NO: 45 for coronavirus OC43.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

Example 1

Genotyping of HPV Using ID Sequence

Using the ID sequences of the present invention, the genes of high-risk HPV (human papilloma virus) types causing cervical cancer were typed.

ID sequences for 15 high-risk HPV types were designed as shown in Table 1 below.

TABLE 1

ID sequences for 15 HPV types

| ID sequences | HPV types |
|---|---|
| AGCACATG | HPV type 16 |
| TGCACATG | HPV type 58 |
| CGCACATG | HPV type 18 |
| GACACATG | HPV type 33 |
| GTCACATG | HPV type 52 |
| GCGACATG | HPV type 35 |
| GCTACATG | HPV type 45 |
| GCATCATG | HPV type 51 |
| GCAGCATG | HPV type 31 |
| GCACTATG | HPV type 39 |

TABLE 1-continued

ID sequences for 15 HPV types

| ID sequences | HPV types |
|---|---|
| GCACGATG | HPV type 56 |
| GCACACTG | HPV type 59 |
| GCACAGTG | HPV type 68 |
| GCACATAG | HPV type 66 |
| GCACATCG | HPV type 82 |

A nucleotide sequence specific to each of 15 HPV types was linked to the 3' terminal end of each of 15 ID sequences, and a common sequencing primer sequence was linked to the 5' terminal end, such that 15 types of different ID sequences can be used in pyrosequencing with a single sequencing primer, thereby constructing PCR primers containing the ID sequences (Table 2).

TABLE 2

ID-sequencing PCR primer mixtures for analysis of HPV genotype - ID sequence-based HPV primers: primers for 15 GT-HPV 15 types GT-HPV 15 type primer construction

| | Sequencing primer binding site | ID sequences | HPV type-specific sequence |
|---|---|---|---|
| HPV type16 (SEQ ID NO: 16) | TAATACGACTCACTATAGGG | AGCACATG | TGTCATTATGTGCTGCCATATC (SEQ ID NO: 1) |
| HPV type58 (SEQ ID NO: 17) | TAATACGACTCACTATAGGG | TGCACATG | ACTGAAGTAACTAAGGAAGG (SEQ ID NO: 2) |
| HPV type18 (SEQ ID NO: 18) | TAATACGACTCACTATAGGG | CGCACATG | ACAGTCTCCTGTACCTGGG (SEQ ID NO: 3) |
| HPV type33 (SEQ ID NO: 19) | TAATACGACTCACTATAGGG | GACACATG | TATGCACACAAGTAACTAGTG (SEQ ID NO: 4) |
| HPV type52 (SEQ ID NO: 20) | TAATACGACTCACTATAGGG | GTCACATG | TGACTTTATGTGCTGAGG (SEQ ID NO: 5) |
| HPV type35 (SEQ ID NO: 21) | TAATACGACTCACTATAGGG | GCGACATG | TGTTCTGCTGTGTCTTCTAG (SEQ ID NO: 6) |
| HPV type45 (SEQ ID NO: 22) | TAATACGACTCACTATAGGG | GCTACATG | CCAAGTACATATGACCCTAC (SEQ ID NO: 7) |
| HPV type51 (SEQ ID NO: 23) | TAATACGACTCACTATAGGG | GCATCATG | ACTGCCACTGCTGCGGTTTC (SEQ ID NO: 8) |

TABLE 2-continued

ID-sequencing PCR primer mixtures for analysis
of HPV genotype - ID sequence-based HPV primers:
primers for 15 GT-HPV 15 types GT-HPV 15 type primer construction

| | Sequencing primer binding site | ID sequences | HPV type-specific sequence |
|---|---|---|---|
| HPV type31 (SEQ ID NO: 24) | TAATACGACTCACTATAGGG | GCAGCATG | CAATTGCAAACAGTGATAC (SEQ ID NO: 9) |
| HPV type39 (SEQ ID NO: 25) | TAATACGACTCACTATAGGG | GCACTATG | AGAGTCTTCCATACCTTCTAC (SEQ ID NO: 10) |
| HPV type56 (SEQ ID NO: 26) | TAATACGACTCACTATAGGG | GCACGATG | TACTGCTACAGAACAGTTAAG (SEQ ID NO: 11) |
| HPV type59 (SEQ ID NO: 27) | TAATACGACTCACTATAGGG | GCACACTG | TGTGCTCTACTACTCTCTATTC (SEQ ID NO: 12) |
| HPV type68 (SEQ ID NO: 28) | TAATACGACTCACTATAGGG | GCACAGTG | ACTACTGAATCAGCTGTACC (SEQ ID NO: 13) |
| HPV type66 (SEQ ID NO: 29) | TAATACGACTCACTATAGGG | GCACATAG | ACTATTAATGCAGCTAAAAGCAC (SEQ ID NO: 14) |
| HPV type82 (SEQ ID NO: 30) | TAATACGACTCACTATAGGG | GCACATCG | TGTTACTCCATCTGTTGCAC (SEQ ID NO: 15) |

The 15 types of HPV viruses were obtained by extracting genomic DNA from Korean female cervicovaginal secretions (Department of Obstetrics & Gynecology, Chungnam National University), identifying the infected genotypes using an HPV DNA chip, and amplifying the L1 gene of the HPV virus by PCR.

As PCR primers for determining whether the clinical samples were infected with HPV, a GP5 plus primer and a GP6 plus primer were used.

TABLE 3

GP5 plus primer/GP6 plus primer

Forward primer

| GP5 plus primer | 5'-TTTGTTACTGTGGTAGATACTAC-3' (SEQ ID NO: 31) |
|---|---|

Reverse primer

| GP6 plus primer | 5'-GAAAAATAAACTGTAAATCATATTC-3' (SEQ ID NO: 32) |
|---|---|

Using each of the 15 types of HPV viruses as a template, PCR amplification was performed under the following conditions using forward primers (15 types of GT-HPV primers) consisting of the 15 types of PCR primers shown in Table 2 and a reverse primer consisting of a 5' biotinylated GP6 plus primer (Bioneer, Korea): 95° C. for 15 min; then 45 cycles each consisting of 95° C. (0.5 min), 45° C. (0.5 min) and 72° C. (0.5 min); then 72° C. (10 min); and then storage at −4° C.

The PCR products contained a common. In this Example, a general T7 primer (5'-TAA TAC GAC TCA CTA TAG GG-3') was used to perform pyrosequencing with the ID sequences, and the pyrograms were analyzed to type HPV (FIGS. 19 and 20).

Figure 19:
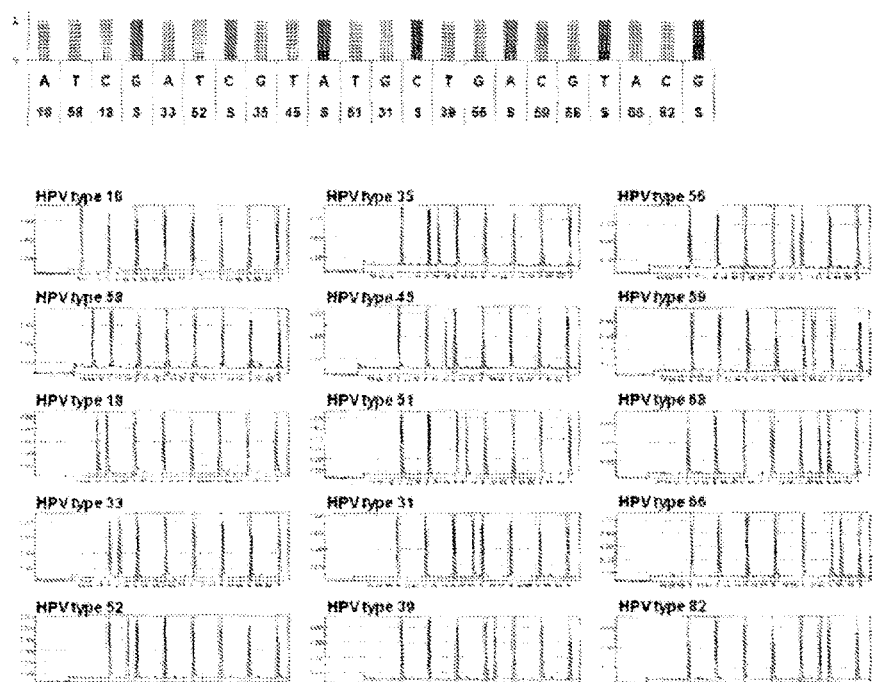
FIG. 19 shows the results obtained by genotyping 15 HPV types using ID sequences of the present invention.
Figure 20:
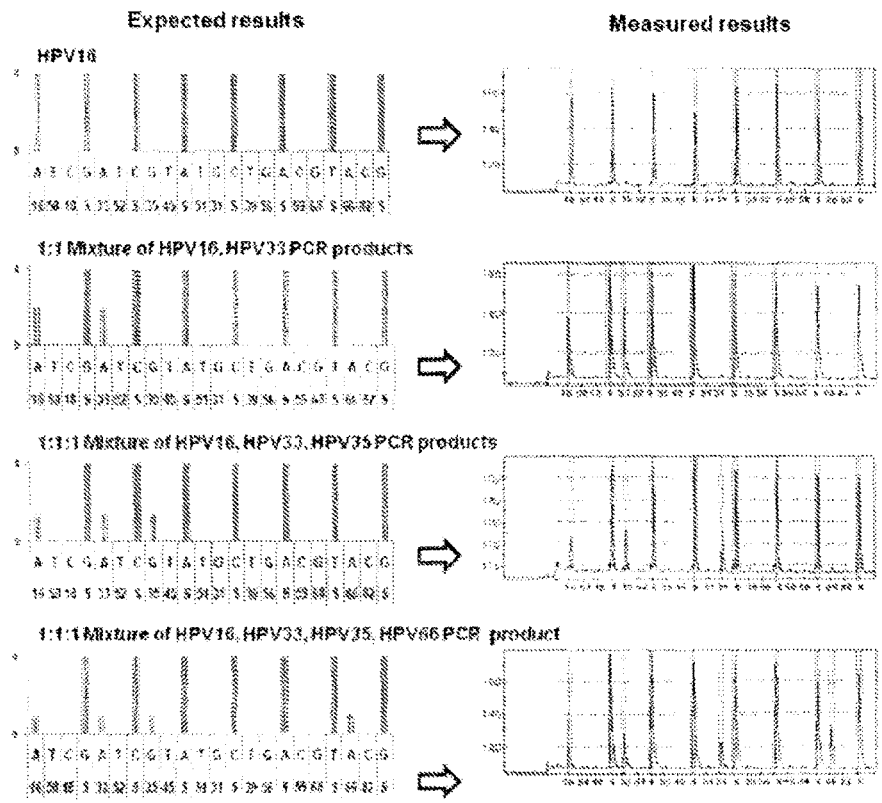
FIG. 20 shows the results obtained by genotyping two or more types of HPV.

The locations of ID marks formed according to the types of HPV in the dispensation order are shown in the upper portion of FIG. 19. In FIG. 19, the peaks indicated in red are ID marks, and the peaks indicated in blue are signposts.

As a result, it could be seen that the pyrogram peaks appeared only in specific ID marks corresponding to the 15 types of HPV viruses.

Example 2

Multiplex HPV Genotyping

Using the HPV ID sequences constructed in Example 1, genotyping of multiple HPV infections was performed.

(1) Multiplex Genotyping of 4 HPV Types

Using the genomic DNA of each of 4 HPV types (HPV 16, 33, 31 and 66) as a template, PCR amplification was performed with the GP5 plus primer and the GP6 plus primer. Then, using a 1:1 mixture of the PCR products for each HPV type as a template, PCR amplification was performed with 15 types of GT-HPV primers and a 5' biotinylated GP6 plus primer. Then, the PCR products were pyrosequenced using a T7 primer.

As a result, as shown in FIG. 20a, the same pyrograms as theoretically expected results could be obtained.

(2) Multiplex HPV Genotyping Using CaSki Cell Line and HeLa Cell Line

Using a mixture of 10 ng of the genomic DNA of the CaSki cell line (ATCC CRL-1550™) infected with HPV type 16 and 10 ng of the genomic DNA of the HeLa cell line (ATCC CCL-2™) infected with HPV 18 as a template, PCR amplification was performed with 15 types of GT-HPV forward primers and a 5' biotinylated GP6 plus primer. Then, the PCR products were pyrosequenced using a T7 sequencing primer to obtain pyrograms for the ID sequences.

As a result, as shown in FIG. 20b, the same pyrograms as theoretically expected results could be obtained, because it is known that CaSki cells contain about 600 copies of HPV type 16 per cell, and HeLa cells contain about 50 copies of HPV type 18 per cells.

(3) Multiplex HPV Genotyping for Cervical Scraps Samples gDNA was extracted from cervical scraps samples was subjected to multiplex HPV genotyping using the ID sequences or to general sequencing. As a result, it could be seen that the results of the multiplex HPV genotyping were completely identical to those of the general sequencing (Tables 4 and 5).

TABLE 4

| Identical | Equal | Total |
|---|---|---|
| 68/79 (86.1%) | 11/79 (13.9%) | 79/79 (100%) |

Summary of comparison between the results of ID sequence-based multiplex HPV genotyping and the results of general sequencing

TABLE 5

Comparison between the results of ID sequence-based multiplex HPV genotyping and the results of general sequencing

| Sample Nos. | ID sequence-based multiplex HPV genotyping | Results of general sequencing |
|---|---|---|
| 1 | 16 | 16 |
| 2 | 66 | 66 |
| 3 | 52 | 52 |
| 4 | 33.68 | 33 |
| 5 | 16 | 16 |
| 6 | 16.68 | 66 |
| 7 | 56 | 56 |
| 8 | 16 | 16 |
| 9 | 66 | 66 |
| 10 | 33 | 33 |
| 11 | 18 | 18 |
| 12 | 18.51 | 51 |
| 13 | 56 | 56 |
| 14 | 16 | 16 |
| 15 | 18 | 18 |
| 16 | 58.66 | 66 |
| 17 | 51 | 51 |
| 18 | 52 | 52 |
| 19 | 58.33 | 33 |
| 20 | 16 | 16 |
| 21 | 16 | 16 |
| 22 | 18 | 18 |
| 23 | 51 | 51 |
| 24 | 56 | 56 |
| 25 | 16 | 16 |

TABLE 5-continued

Comparison between the results of ID sequence-based multiplex HPV genotyping and the results of general sequencing

| Sample Nos. | ID sequence-based multiplex HPV genotyping | Results of general sequencing |
|---|---|---|
| 26 | 58 | 58 |
| 27 | 18 | 18 |
| 28 | 52 | 52 |
| 29 | 16 | 16 |
| 30 | 33 | 33 |
| 31 | 58 | 58 |
| 32 | 16 | 16 |
| 33 | 16 | 16 |
| 34 | 16 | 16 |
| 35 | 16 | 16 |
| 36 | 33 | 33 |
| 37 | 18 | 18 |
| 38 | 56 | 56 |
| 39 | 16 | 16 |
| 40 | 16 | 16 |
| 41 | 35 | 35 |
| 42 | 16 | 16 |
| 43 | 35 | 35 |
| 44 | 58 | 58 |
| 45 | 35 | 35 |
| 46 | 16.52 | 52 |
| 47 | 33 | 33 |
| 48 | 16.31 | 16 |
| 49 | 58 | 58 |
| 50 | 58 | 58 |
| 51 | 16 | 16 |
| 52 | 33 | 33 |
| 53 | 16.51 | 51 |
| 54 | 16 | 16 |
| 55 | 16 | 16 |
| 56 | 18.31 | 31 |
| 57 | 16 | 16 |
| 58 | 16 | 16 |
| 59 | 58 | 58 |
| 60 | 16 | 16 |
| 61 | 16.58 | 16 |
| 62 | 16 | 16 |
| 63 | 33 | 33 |
| 64 | 16.56 | 16 |
| 65 | 18 | 18 |
| 66 | 16 | 16 |
| 67 | 16 | 16 |
| 68 | 58 | 58 |
| 69 | 16 | 16 |
| 70 | 16 | 16 |
| 71 | 33 | 33 |
| 72 | 16 | 16 |
| 73 | 16 | 16 |
| 74 | 16 | 16 |
| 75 | 16 | 16 |
| 76 | 58 | 58 |
| 77 | 16 | 16 |
| 78 | 58 | 58 |
| 79 | 16 | 16 |

Example 3

Detection of KRAS Mutations Using ID Sequences

In order to detect mutations in the KRAS gene using the ID sequences of the present invention, ID sequences for three types of KRAS mutations, that is, mutations of codon 12 (GGT>GTT) and codon 13 (GGC>TGC and GGC>GCC), were designed (Table 6).

TABLE 6

ID sequences for three types of KRAS mutations

| | ID sequences | KRAS mutation types |
|---|---|---|
| ID1 | GTGC<u>A</u>GT | codon12 (GGT > GTT) |
| ID2 | GTGC<u>T</u>GT | codon13 (GGC > TGC) |
| ID3 | GTGCG<u>A</u>T | codon13 (GGC > GCC) |

In addition, a nucleotide sequence specific to each of the three types of KRAS mutations was linked to the 3' terminal end of each of the ID sequences, and a common sequencing primer sequence to the 5' terminal end, such that pyrosequencing can be performed using the three different ID sequences with a single sequencing primer, thereby constructing ID sequence-containing PCR primers (Table 7).

TABLE 7

ID sequence-based KRAS primers: GT-KRAS ID primers

GT-KRAS ID forward primer

| | Sequencing primer binding site | ID sequence | KRAS mutation-specific sequence |
|---|---|---|---|
| Codon12 (GGT > GTT) (SEQ ID NO: 36) | AACTTGTGGTAGTT-GGAGCT | GTGCAGT | TGGAGCTGT (SEQ ID NO: 33) |
| Codon13 (GGC > TGC) (SEQ ID NO: 37) | AACTTGTGGTAGTT-GGAGCT | GTGCTGT | GAGCTGGTT (SEQ ID NO: 34) |
| Codon13 (GGC > GCC) (SEQ ID NO: 38) | AACTTGTGGTAGT-TGGAGCT | CGCA-CATT | AGCTGGTGC (SEQ ID NO: 35) |

Templates for mutations corresponding to the ID sequences used as samples were made through gene synthesis (Bioneer, Korea), and the normal KRAS cell line Caco2 (ATCC HTB-37) and the mutant cell lines A549 (ATCC CCL-185) and HCT116 (ATCC CCL-247) were used.

TABLE 8

KRAS PCR primers

Forward primer

| KRAS-F (SEQ ID NO: 39) | 5'-NNNGGCCTGCTGAAAATGACTGAA-3' |
|---|---|

Reverse primer)

| KRAS-R (SEQ ID NO: 40) | 5'-TTAGCTGTATCGTCAAGGCACTCT-3' |
|---|---|

Each of the templates was amplified by PCR using the four types of KRAS forward primers and a 5' biotinylated reverse primer, and the PCR products were pyrosequenced under the following conditions:

95° C. for 5 min, then 40 cycles of 95° C. (0.5 min), 60° C. (0.5 min) and 72° C. (0.5 min), then 72° C. (10 min, and then storage at −4° C.

Figure 21:
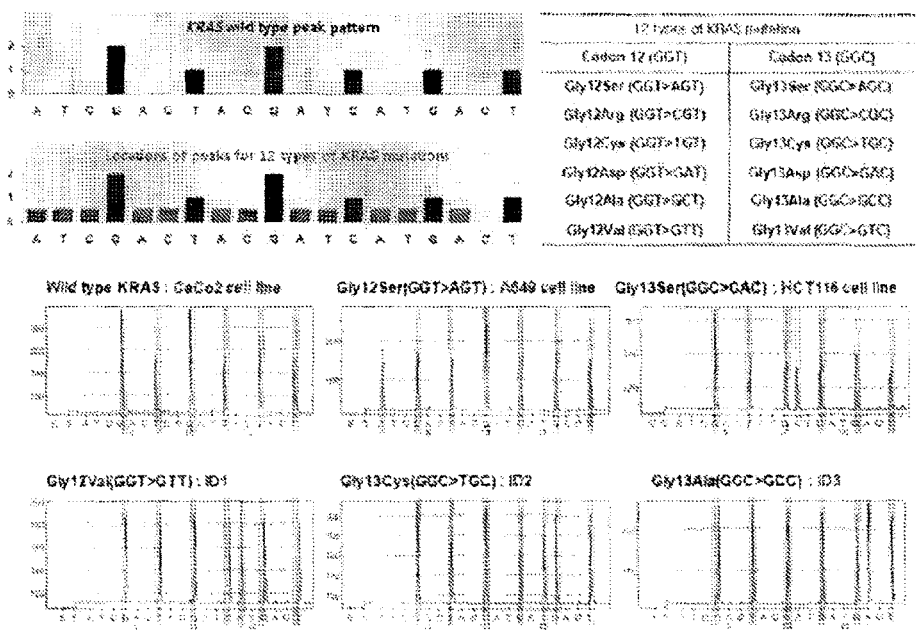
FIG. 21 shows the results of detecting KRAS mutations using ID sequences of the present invention.

Using each of the normal KRAS cell line and a KRAS mutant plasmid from the mutant cell lines as a template, KRAS mutations were detected using the ID sequences (FIG. 21).

As a result, it could be seen that pyrogram peaks appeared in the specific ID marks corresponding to the mutant strains.

In order to examine whether the detection of multiple mutations can be achieved by the ID sequence-based KRAS mutation method, the three types of KRAS mutant DNAs were mixed at the same ratio, followed by pyrosequencing for detection of KRAS mutations.

Figure 22:
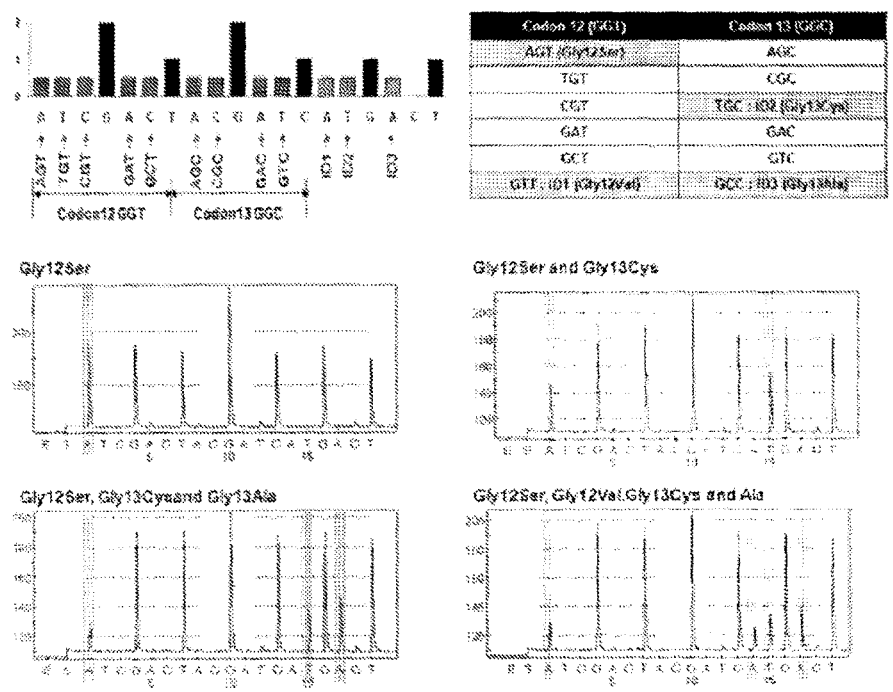
FIG. 22 shows the results of detecting multiple KRAS mutations using ID sequences of the present invention.

As a result, as can be seen in FIG. 22, the same pyrograms as theoretically expected results were obtained.

Figure 23:
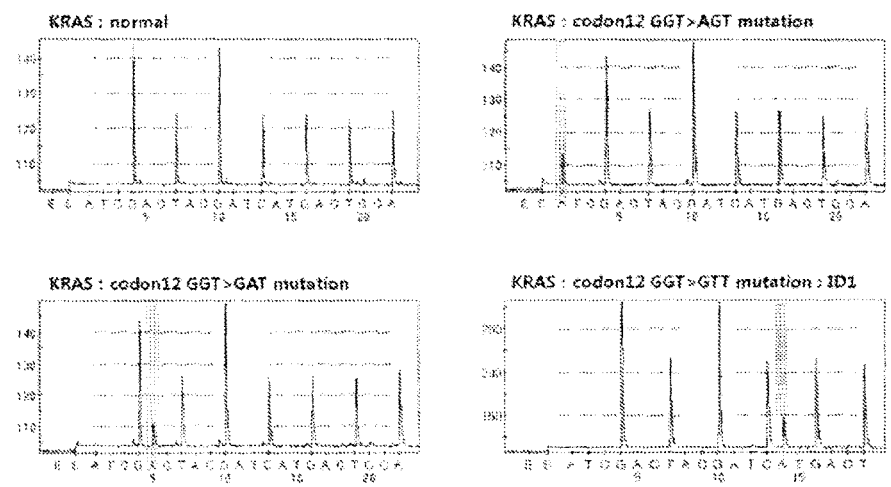
FIG. 23 shows the results of detecting KRAS mutations in colorectal cancer tissue using ID sequences of the present invention.

In addition, whether the ID sequence-based KRAS multiple mutation detection method can be applied to actual clinical samples was tested using gDNA of colorectal tissue samples from 12 colorectal cancer patients. As a result, mutations could be detected in 3 patients, and typical pyrograms for the mutations are shown in FIG. 23.

Example 4

Detection of Respiratory Virus Infections Using ID Sequences

New influenza A (H1N1) and seasonal influenza A (H1 and H3) and B viruses prevail in the same season and show similar infection symptoms, but show different responses to antiviral agents. Thus, it is required to accurately identify virus types for treatment. Thus, in the present invention, a method of genotyping respiratory virus using the ID sequence was developed.

In this Example, detection of typical respiratory viruses, influenza A virus, influenza B virus, RSV B, rhinovirus and coronavirus OC43, was performed. ID sequences for the 5 types of respiratory viruses were designed as shown in Table 9 below.

TABLE 9

ID sequences for five types of respiratory viruses

| ID sequence | Kind of respiratory viruses |
|---|---|
| CATA | Influenza A virus |
| GATA | Influenza B virus |
| TATA | RSV B |
| ACTA | Rhino virus1 |
| ATCA | *Coronavirus* OC43 |

A nucleotide sequence specific to each of the 5 types of respiratory viruses was linked to the 3' terminal end of each of the ID sequences, and a common sequencing primer sequence was linked to the 5' end, pyrosequencing for the 5 types of ID sequences can be performed using a single sequencing primer, thereby constructing ID sequence-containing PCR primers (Table 10).

TABLE 10

ID sequence-based respiratory virus forward
primers: GT-RespiVirus ID primers

GT- respiratory virus 5 type primer construction

| | Sequencing primer binding sites | ID sequence | Respiratory virus-specific sequence |
|---|---|---|---|
| Influenza A virus (SEQ ID NO: 46) | TAATACGACTCACTATA-GGG | CATA | ATATACAACAGGATGGGGGCTGTG (SEQ ID NO: 41) |
| Influenza B virus (SEQ ID NO: 47) | TAATACGACTCACTATA-GGG | GATA | ATCATCATCCCAGGCGACAAAGATG ((SEQ ID NO: 42) |
| RSV B (SEQ ID NO: 48) | TAATACGACTCACTATA-GGG | TATA | TGATATGCCTATAACAAATGACCAGAAA (SEQ ID NO: 43) |
| Rhino virus1 (SEQ ID NO: 49) | TAATACGACTCACTATA-GGG | ACTA | GCCAGAAAGTGGACAAGGTGTGAAGAG (SEQ ID NO: 44) |
| Coronavirus OC43 (SEQ ID NO: 50) | TAATACGACTCACTATA-GGG | ATCA | GCAGATTTGCCAGCTTATATGACTGTT (SEQ ID NO: 45) |

Figure 24:
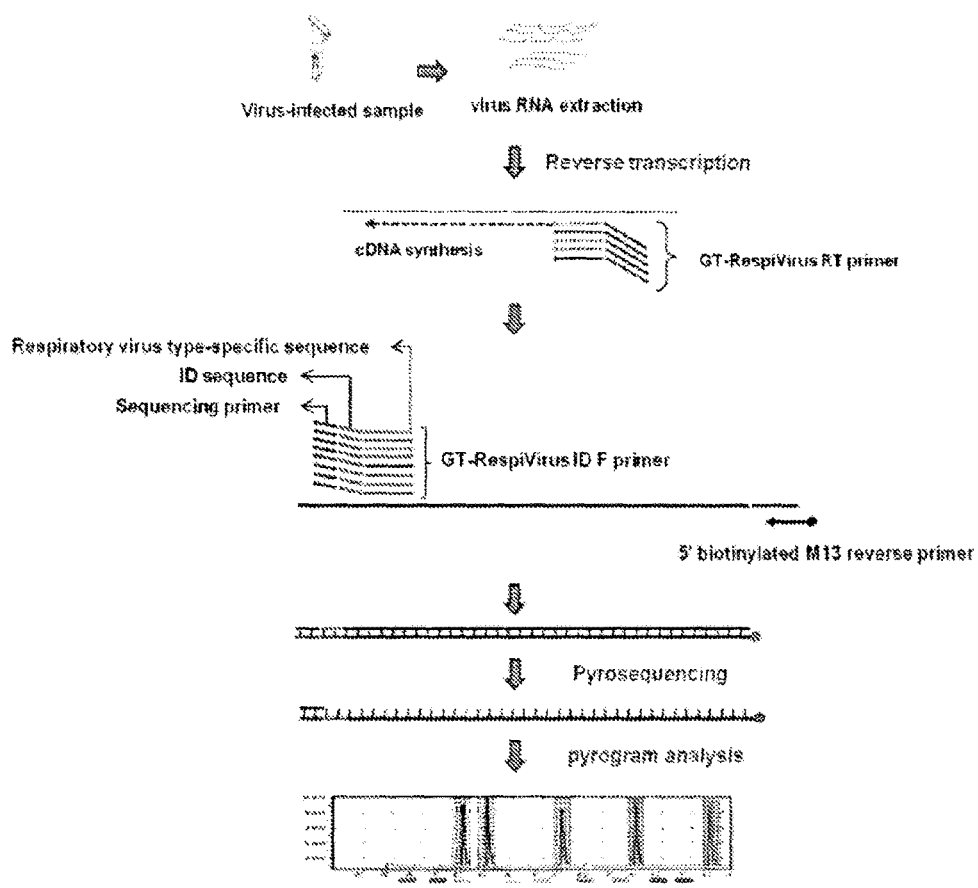
FIG. 24 shows a method of detecting respiratory virus infection using an ID sequence of the present invention.

In the respiratory virus detection method of this Example, cDNAs from virus-infected cells were synthesized using the 5 types of GT-respiratory forward primers and a 5' biotinylated reverse primer (Table 11), and then amplified by PCR using the GT-RespiVirus ID primers shown in Table 10 and a 5' biotinylated M13 reverse primer. The PCR products were pyrosequenced to detect virus infection (FIG. 24).

In this Example, the required portions of the virus genes were synthesized, and multiplex PCR was performed using the synthesized virus genes as templates, followed by pyrosequencing for detection of the virus genes.

Figure 25:
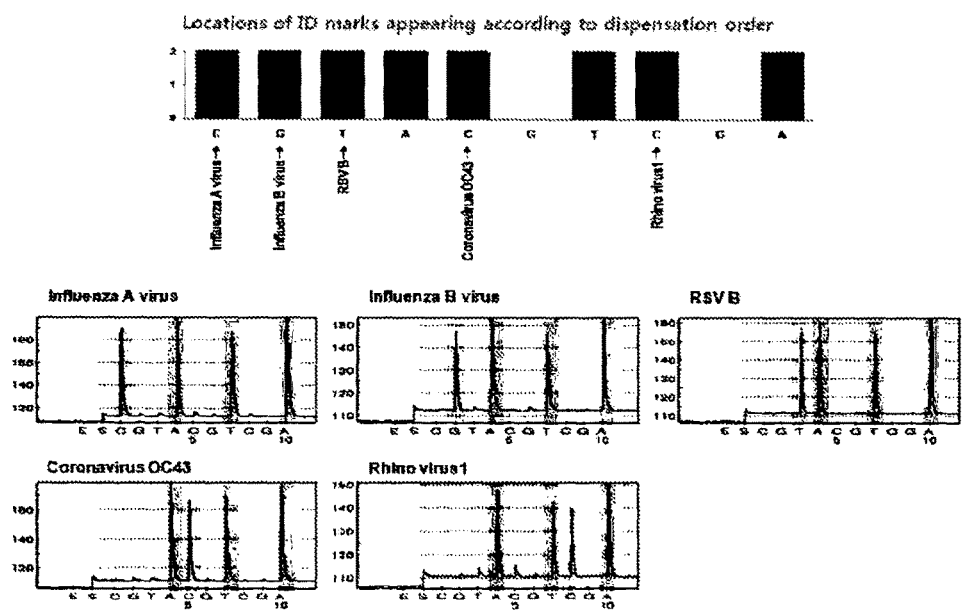
FIG. 25 shows the results of detecting single infections of 5 types of respiratory viruses using ID sequences of the present invention.
Figure 26:
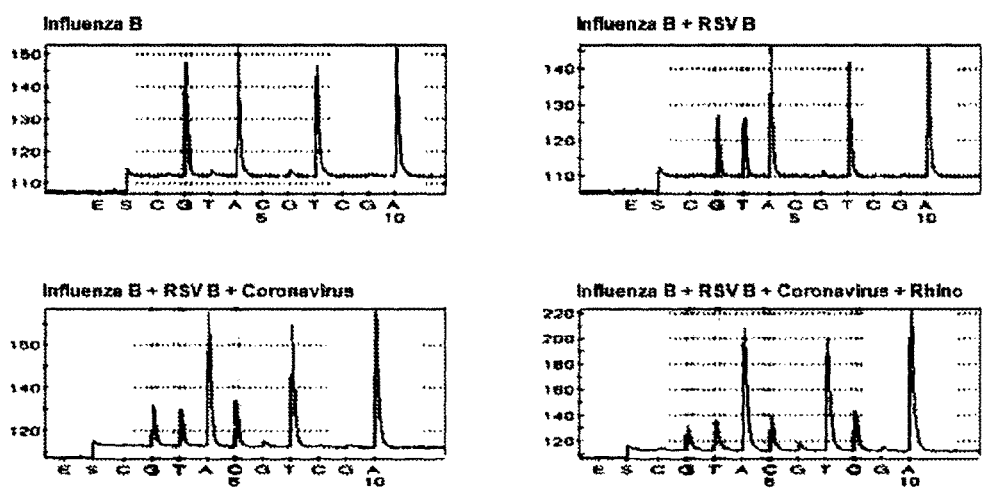
FIG. 26 shows the results of detecting multiple infections of 5 types of respiratory viruses using ID sequences of the present invention.

As a result, as can be seen in FIG. 25, the same pyrograms as theoretically expected results could be obtained.

In addition, in a test for detection of multiple infections, the virus gene templates were mixed at the same ratio, and

TABLE 11

ID sequence-based respiratory virus reverse
transcription (RT) primers: GT-RespiVirus RT primers GT-RespiVirus RT R primer construction

| | M13 R Tagging sequence | respiratory virus type-specific sequence |
|---|---|---|
| Influenza A virus (SEQ ID NO: 51) | CAGGAAACAGCTATGACC | ATATACAACAGGATGGGGGCTGTG |
| Influenza B virus (SEQ ID NO: 52) | CAGGAAACAGCTATGACC | ATCATCATCCCAGGCGACAAAGATG |
| RSV B (SEQ ID NO: 53) | CAGGAAACAGCTATGACC | TGATATGCCTATAACAAATGACCAGAAA |
| Rhino virus1 (SEQ ID NO: 54) | CAGGAAACAGCTATGACC | GCCAGAAAGTGGACAAGGTGTGAAGAG |
| Coronavirus OC43 (SEQ ID NO: 55) | CAGGAAACAGCTATGACC | GCAGATTTGCCAGCTTATATGACTGTT | then amplified by multiplex PCR, followed by pyrosequencing for detection of the viral genes. As a result, multiple infections were normally detected.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

When pyrosequencing is performed using the ID sequence, a unique and simple pyrogram can be obtained for each genotype. Thus, the use of the ID sequence makes it possible to genotype viral genes, disease genes, bacterial genes and identification genes in a simple and efficient manner.

What is claimed is:

1. A method of genotyping for target genes which comprises
   i) synthesizing a primer set comprising plural primers for multiplex genotyping different target sequences in a sample with sequencing by DNA synthesis, wherein each primer consists of:
   a) a sequencing primer located at 5' end of each primer;
   b) a target-specific sequence located at 3' end of each primer; and
   c) an ID sequence located between a sequencing primer sequence and a target-specific sequence in each primer, wherein each ID sequence consists of 5'-ID mark-$S_N$-E-3' or 5'-$S_N$-ID mark-$S_N$-E-3':
   (1) an ID mark which is a single nucleotide selected from the group consisting of A, T, C and G that should be separated as a different genotype;
   (2) N signposts (S), wherein signposts consist of a nucleotide or nucleotides, in which a nucleotide is different from the next 3' ended and 5' ended nucleotides and the nucleotide or 5' end terminal nucleotide of signposts is different from the next ID mark; and
   (3) endmark (E) which is a single nucleotide following most 3' end terminal signpost and different from the most 3' end terminal signpost;
   wherein N is a natural number ranging from 2 to 32, and wherein the ID mark is different from the next signpost located 3'end of the ID mark
   ii) amplifying, by multiplexing amplification, target genes by PCR using primers synthesized in i), thereby obtaining PCR products, wherein the signposts (S) in primers in the set have identical nucleotide sequences;
   iii) sequencing the PCR product to obtain a signal for the ID sequence of each genotype; and
   iv) genotyping according to the nucleotide and location of the ID mark,
   wherein the number of primers in the primer set for said genotyping for target genes is designed according to the number of signposts based on (2N +1) (N is the number of S).

2. The method of claim 1, wherein step iii) comprises sequencing the PCR products of step ii) based on the sequencing by DNA synthesis with dispensation of dNTPs according to the order of the ID sequences of the step i), in which dNTP for the endmark is not included.

3. The method of claim 1, wherein the target genes are selected from the group consisting of viral genes, disease genes, bacterial genes.

4. The method of claim 1, wherein the target is HPV and wherein the target specific sequence is selected from the group consisting of nucleotide sequences of SEQ ID NOs: 1 to 15.

5. The method of claim 1, wherein the target is a respiratory virus and wherein the target specific sequence is SEQ ID NO:41 for influenza A virus, SEQ ID NO: 42 for influenza B virus, SEQ ID NO:43 for RSV B, SEQ ID NO:44 for rhinovirus, or SEQ ID NO:45 for coronavirus OC43.

* * * * *